(12) United States Patent
Scott et al.

(10) Patent No.: US 11,987,602 B2
(45) Date of Patent: May 21, 2024

(54) MALONATE TRANSPORTERS

(71) Applicant: CB Therapeutics, Inc., Carlsbad, CA (US)

(72) Inventors: Erin Marie Scott, Encinitas, CA (US); Jacob Michael Vogan, San Diego, CA (US)

(73) Assignee: CB Therapeutics, Inc., Carlsbad, CA (US)

( * ) Notice: Subject to any disclaimer, the term of this patent is extended or adjusted under 35 U.S.C. 154(b) by 603 days.

(21) Appl. No.: 17/349,640

(22) Filed: Jun. 16, 2021

(65) Prior Publication Data

US 2021/0388035 A1 Dec. 16, 2021

Related U.S. Application Data

(62) Division of application No. 16/558,973, filed on Sep. 3, 2019, now Pat. No. 11,041,002.

(51) Int. Cl.
| | |
|---|---|
| *C12N 15/80* | (2006.01) |
| *C07K 14/21* | (2006.01) |
| *C12P 7/22* | (2006.01) |
| *C12P 7/42* | (2006.01) |
| *C12P 17/06* | (2006.01) |

(52) U.S. Cl.
CPC .............. *C07K 14/21* (2013.01); *C12N 15/80* (2013.01); *C12P 7/22* (2013.01); *C12P 7/42* (2013.01); *C12P 17/06* (2013.01); *C12Y 121/03007* (2015.07); *C12Y 121/03008* (2015.07)

(58) Field of Classification Search
CPC ......... C07K 14/21; C12N 15/80; C12P 17/06; C12P 7/22
See application file for complete search history.

(56) References Cited

U.S. PATENT DOCUMENTS 11,041,002 B1 * 6/2021 Scott ........................ C12P 7/22

* cited by examiner

*Primary Examiner* — Tekchand Saidha
(74) *Attorney, Agent, or Firm* — Gendloff IP; Elie Gendloff

(57) ABSTRACT

The methods and systems disclose enzymes that function to import malonic acid or malonates into a cell. The enzymes increase the output of precursor molecules by enriching certain pathways in the cell. The precursor molecules can be converted to cannabinoids. The enzymes are a family of proteins which have a majority of common alignments.

13 Claims, 11 Drawing Sheets

Specification includes a Sequence Listing.

| Full Name | Abbreviation (3 Letter) | Abbreviation (1 Letter) |
|---|---|---|
| Alanine | Ala | A |
| Arginine | Arg | R |
| Asparagine | Asn | N |
| Aspartate | Asp | D |
| Aspartate or Asparagine | Asx | B |
| Cysteine | Cys | C |
| Glutamate | Glu | E |
| Glutamine | Gln | Q |
| Glutamate or Glutamine | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

FIG. 1

```
                  1       10        20        30        40        50        60        70        80        90       100       110       120       130
                  |--------+---------+---------+---------+---------+---------+---------+---------+---------+---------+---------+---------+---------|
   S_pombe_mae1   MGELKEITLK--QRYHELLDWNYKAPHVPLSQRLKHFTWSWFACTMATGGVLIIGSFPRFYGLNTIGKIVYILQIFLFSGSCMLFRFIKYPSTIKDSWNHHLEKLFIATCLLSISTFIDMLAIYAYP
 S_cryophilus_MAE1 MADVKGMLR--QRYHELLDWQVKSPHVPLSQRIKHFTWSWFACTMATGGLVIGTFPFRGLDTIGKIVYIFDIFLLALFSCCMIVRFVKYPGTFLGSWKHFQEKFFIATCLLSFSSFIDMFAVYAMP
 S_japonicus_MAE1  MGELKEILKSSQRYNELIAWNVKGPRLPIAQRLKHFTWSWFTCTMATGGVGMILASLPYRFTGLNTIGKVVFIFQVVLAIFCSAMAFRFIRYPETFKKSIYHHLEKLFIGTFLLSMSTFIDMLAAYGYP
        Consensus Mg#1KeiLk..QRYhEL1dW#VK.PhvP1sQR1KHFTWSWFaCTMATGG!G$!igsfP%RF.GL#TIGK!V%!if##!L1a1F.scM.fRF!kYP.Tfk.Sw.Hh1EK1F!aTcLLs.S!FIDM1A.YayP 131     140       150       160       170       180       190       200       210       220       230       240       250       260
                  |--------+---------+---------+---------+---------+---------+---------+---------+---------+---------+---------+---------+---------|
   S_pombe_mae1   DTGEWMVWVIRILYYIYVAVSFIYCVMAFFTIFNNHVYTIETASPAWILPIFPPMICGVIAGAVNSTOPAHQLKNMVILGIMFQGLGFWVYLLLFAVNVLRFFTVGLAKPQDRPGMFMFVGPPAFSGLAL
 S_cryophilus_MAE1 NTGEWMIWVIRIFFYIYLAVTFLYGTFAYYTIFRDHVYTLEGAAPTWVLPIFPCMITGVWSGSVWSSOPSAQLKNMVILGIMFQGLGFWVYLLVYSILILRFFTIGFAKPAERPGMFILVGPAGFTGLAL
 S_japonicus_MAE1  STGEWMVYLIRIFWWYFAYSFIYYAFAFATTFHMHPYTTLETASPAWILPIFPAMISGAVAGTVAFTQPPHQLKNLVVCGMFQGLGFWVYIMLFAVNMILKLFTKGMMGASERPGLFMFVGPPAYTGLAL
        Consensus .TGEWM!wvIRIf%yiY.AVsF.Y..fA%.TIF..HvYTIE!AsPaWlLPIFP.MI.Gv!aG.V..stQP.hQLKN$V!.GI$FQGLGFWVY1$1%aln.LrfFT.G.akp.#RPG$FmfVGPpa%tGLAL 261     270       280       290       300       310       320       330       340       350       360       370       380       390
                  |--------+---------+---------+---------+---------+---------+---------+---------+---------+---------+---------+---------+---------|
   S_pombe_mae1   INIARGAMGSRPYIFVGAN-SSEYLGFVSTFMAIFIWGLAAWCYCLAMVSFLAGFFTRAPLKFACGWFAFIFPNVGFVNCTIEIGKMIDSKAFQMFGHIIGVILCIQWILLMYLMVRAFLVNDLCYPGKD
 S_cryophilus_MAE1 INMARGAIATRPNIFASAN-SSEYFAFTSTFLALFIWGLGAAWTYCFAMVSFVAGLFSHOPMKFSNTWFAMIFPNYGFVLCTVRIGQMINSKAFTLFGHICVILCIMNILLMWMMIRAFLVNDLMYPGKD
 S_japonicus_MAE1  IGMGKTAMDSKISMJFSATPVSSEHLAFMCTFMALFMWGLAAWCYCVAMVCFAAGFMSRAPIQFKLGWFAFIFPVVGFVNVTMKIGEMIDSAAFKIFGRIYIGAMLAIQWMFyMFFMVRAVLLQEIMYPGRD
        Consensus InmargAm.srp.iF..an.SSEyiaF.sTF$A1FIWGLaAWcYC.AMVsF.AG!fsraP.KF..gWFAflFPnVGFVncT..IG.MI#SKAF..FGH!.lgv!cIW..1M%..M!RAfLv##ImYPGKD 391     400       410       420       430       440444
                  |--------+---------+---------+---------+---------+-----|
   S_pombe_mae1   EDAHPPPKPNTGVLNPTFPPEKAPASLEKVDTHVTSTGGESDPPSSEHESV
 S_cryophilus_MAE1 EDSKSPAESRPIAVEPEKFGIPKSOPENSLDVEKADNPLDSANHGADHDRDSSS
 S_japonicus_MAE1  EDVKTPPGATPPPTLVTSPLSFASLQDVKDGHPIQVTVSRTRDRSKQHMS
        Consensus ED.k.Pp...p....pt.p...as....k.d......t...s...s.#H.s....
```

FIG. 4

```
                      1       10        20        30        40        50        60        70        80        90       100       110       120       130
                      |--------+---------+---------+---------+---------+---------+---------+---------+---------+---------+---------+---------+---------|
   Kluyveromyces_lactis MAAESIYSRDESIASLEKAEGRITYLKPQSRITHSDAKKYLATRIPTLFPTKASIREARKEYPINPFPALRSMNHLQTQYFIYGFLAHTHDALDFFAYSLNMTNLAKDLDRPYKDISHAITLYLLLRYIG
   Kluyveromyces_dobzra MAADSIYSQEESYYSYDKAEGRITYLKPQSQITHSDAKHYLGTRLPTLFPTKRSIKEARKHYPLNPFPALRSMNHLQTQYFLYGFLAHTHDALDFFAYSLNMTNLARDLDRPYKDISHAITLYLLLRYYG
             Consensus MAA#SIYS#ES!aS!KAEGRITYLKPQSQiTHSDAKHYLSTRIPTLFPTKaSINEARKEYPINPFPALRSMNHLQTQYFPYGFLAHTHDALDFFAYSLNMTNLARDLDRPYKDISHAITLYLLLRYIG 131     140       150       160       170       180       190       200       210       220       230       240       250       260
                      |--------+---------+---------+---------+---------+---------+---------+---------+---------+---------+---------+---------+---------|
   Kluyveromyces_lactis ALIFGYLGDRYGRKYSFYLTMALIIYIQIGTGFYNSFSAFLGCRAIFGIIMGSYFGYASATALENAPNKAKSILSGIFQEGYAFGYLLGYYFQRAIYDNSPHGRAIFHFSAGPPYLFIAHRLMLPESQH
   Kluyveromyces_dobzra ALIFGYLGDRYGRKYSFYATMYLIYIQIGTGFYTTFSAFLGCRAIFGIIMGSYFGYASATSLENAPHKAKSILSGIFQEGYAFGYLLGYYFQRAIYDNSPHGRAMFHFSSCPPYLFIAHRLMLPESQH
             Consensus ALIFGYLGDRYGRKYSFYaTMaLIIIQIGTGFYnsFSAFLGCRAIFGIIMGSYFGYASATALENAPaKAKSILSGIFQEGYAFGYLLGYYFQRAIYDNSPHGRAIFHFSaGPPYLFIAHRLMLPESQH 261     270       280       290       300       310       320       330       340       350       360       370       380       390
                      |--------+---------+---------+---------+---------+---------+---------+---------+---------+---------+---------+---------+---------|
   Kluyveromyces_lactis YVERYRLEKLENDGKSQFHKNAKLACSQYHLSMIYLYLLMAGENESSHGSQDLFPTMLTSQYQFSADASTYTNSYANLGAIAGGIIYAHASSFFGRRFSIIYCCIGGGAMLYPHGFYANKSGINASYFFL
   Kluyveromyces_dobzra YLERYRLEKLENDGESQFHKNAKLACSQYHLSMYYLYLLMAGNFSSHGSQDLFPTMLTSQYQFSADASTYTNSYANLGAIAGGIIYAHSSSFIGRRFAILLCCIGGGAMLYPHGFIANKSGLNASYFFL
             Consensus YlERYRLEKLENDGESQFHKNAKLACSQYHLSMIYLYLLMAGENESSHGSQDLFPTMLTSQYQFSADASTYTNSYANLGAIAGGIIYAH.SSFGRRFaliICCIGGGAMLYPHGF.IANKSGINASYFFL 391     400       410       420       430       440       450       460       470       480       490       500       510       520
                      |--------+---------+---------+---------+---------+---------+---------+---------+---------+---------+---------+---------+---------|
   Kluyveromyces_lactis QFFYQGAHGIYPIHLTELAPTEFRALITGYAYQLGNMISSASSTIEASIGERFPLEGREDAYDYGKYMCIFMGCYFAYLLIYTYLGPENKGGELRLSTTGTEQDDEESQNNISFEEIYAAGPYSDLNFKQ
   Kluyveromyces_dobzra QFFYQGAHGIYPIHLTELAPAEFRALITGYAYQLGNMISSASSTIEATLGEKFPIEGREGAYDYGKYMCIFMGCYFAYLLIITYLGPENKGGELRLSSPGMIE-DDYESQNNVYSFERYGEIQPASELNEKQ
             Consensus QFFYQGAHGIYPIHLTELAPAEFRALITGYAYQLGNMISSASSTIEAsiGETFPIEGREJAYDYGKYMCIFMGCYFAYLLI!TYLGPENKGGELRLSspGnE.DDEESQNNISFErl.gaapPaS#LNFKQ 521     528
                      |--------|
   Kluyveromyces_lactis EIQHKERY
   Kluyveromyces_dobzra EIQHKERY
             Consensus EIQHKERY
```

MALONATE TRANSPORTERS

CROSS-REFERENCE TO RELATED APPLICATIONS

This is a divisional application of application Ser. No. 16/558,973, filed Sep. 3, 2019, and incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 30, 2021, is named CBTH-04-DIV1_SL.txt and is 37,262 bytes in size.

INCORPORATION-BY-REFERENCE OF MATERIAL SUBMITTED

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The ASCII text file, entitled "SeqMALONATETRANSPORTERS.txt" was created on Oct. 27, 2019 using PatentIn version 3.5 and is incorporated herein by reference in its entirety. The subject matter of the Sequence Listing is incorporated herein by reference in its entirety.

FIELD

The present invention generally relates to the production of cannabinoids in a heterologous cell and to methods for improving production of these molecules by genetically modifying the host organism. More specifically, a malonate transporter enzyme is overexpressed to facilitate import of malonic acid or its salt malonate. This improves titers of cannabinoid molecules, wherein malonic acid is a precursor of cannabinoids that is directly incorporated into cannabinoids during biosynthesis. The process occurs in genetically engineered host cell(s) that can produce cannabinoids.

INTRODUCTION

Cannabinoids, which are organic small molecules being investigated for treatment for chronic pain, multiple sclerosis, and epilepsy, may be obtained via biosynthesis. The biosynthesis of cannabinoids can take place in plants, microorganisms (e.g., bacteria, algae, fungi (yeast and mold), protozoa, and viruses). Malonic acid ($C_3H_4O_4$, CAS Number 141-82-2), which also is referred to as propanedioic acid or methanedicarboxylic acid, is a dicarboxylic acid that is a competitive inhibitor of succinic dehydrogenase in the Krebs cycle.

Coenzyme A reacts with malonic acid and acetyl-CoA to yield Malonyl-CoA ($C_{24}H_{38}N_7O_{19}P_3S$, CAS Number 524-14-1) and Acetyl-CoA ($C_{23}H_{38}N_7O_{17}P_3S$, CAS Number 72-89-9), respectively. Malonyl-CoA and acetyl-CoA are precursors for fatty acid biosynthesis and polyketide biosynthesis. More specifically, malonyl-CoA is highly regulated molecule in fatty acid synthesis and thereby inhibits the rate-limiting step in the beta-oxidation of fatty acids. Carnitine is inhibited from associating with malonyl-CoA by regulating the enzyme carnitine acyltransferase. In turn, the fatty acids and carnitine are prevented from entering into mitochondria for oxidation or degradation of fatty acids.

Genetic modifications may allow cells to uptake carbon sources, such as sugars, small molecule carbon substrates (e.g., malonic acid, malonate derivatives, acetyl derivatives), and co-feed biomass systems, for conversion into useable precursors for the production of cannabinoids more efficiently. The genetic modifications are directed to genes encoding proteins, such as enzymes, involved in cannabinoid biosynthesis. Accordingly, the genetic modifications can increase the output of cannabinoids by altering the production capacity of the cell from the natural state of the cell.

Features, aspects, and advantages of the present teachings will become better understood with reference to the following description, examples and appended claims.

SUMMARY

The present teachings include methods for increasing production of cannabinoid molecules in a host cell. The method can include: expressing a family of genes; inserting the family of genes into the host cell and thereby enhancing a level of malonate transporters in the host cell; suppressing the first pathway in the host cell while enriching the second pathway in the host cell by enhancing the level of malonate transporters in the cell; and enhancing titers of a product commencing at the second pathway in the host cell. The family of genes may comprise at least nine nodes divided among a plurality of generations in a phylogenetic network. The host cell comprises at least a first pathway and a second pathway;

In the method for increasing production of cannabinoid molecules in the host cell, host cell can derive from an organism. The organism can be selected from *Schizosaccharomyces japonicus*, *Schizosaccharomyces pombe*, *Schizosaccharomyces cryophilus*, *Saccharomyces cerevisiae*, *Kluyveromyces lactis*, and *Kluyveromyces dobzhanskii*.

In the method for increasing production of cannabinoid molecules in the host cell, the malonate transporters can comprise SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

In the method for increasing production of cannabinoid molecules in the host cell, SEQ ID NO: 1, SEQ ID NO: 2, and SEQ ID NO: 3 can include a first set of shared elements.

In the method for increasing production of cannabinoid molecules in the host cell, SEQ ID NO: 6 and SEQ ID NO: 7 can include a second set of shared elements.

In the method for increasing production of cannabinoid molecules in the host cell, SEQ ID NO: 1, SEQ ID NO: 2, SEQ ID NO: 3, SEQ ID NO: 4, SEQ ID NO: 6, SEQ ID NO: 7, and SEQ ID NO: 8 can include respective sequences encoded by a first polypeptide.

In the method for increasing production of cannabinoid molecules in the host cell, SEQ ID NO: 9, SEQ ID NO: 10, SEQ ID NO: 11, and SEQ ID NO: 12 can include: (i) respective sequences encoded by a second polypeptide and a third polypeptide; and (ii) a first subunit and a second subunit.

In the method for increasing production of cannabinoid molecules in the host cell, SEQ ID NO: 9 and SEQ ID NO: 10 can include alignments along the first subunit.

In the method for increasing production of cannabinoid molecules in the host cell, SEQ ID NO: 11 and SEQ ID NO: 12 can include alignments along the second subunit.

In the method for increasing production of cannabinoid molecules in the host cell, the family of genes can include genes selected from MAE1, JEN2, OAC1, OAC1 delta N28, MadM, MdcM, MadL, and MdcL.

In the method for increasing production of cannabinoid molecules in the host cell, the product is olivetol, olivetolic acid, derivatives of olivetol, or derivatives of olivetolic acid.

In the method for enhancing titers of the product commencing at the second pathway in the host cell can include: reacting the product with a first intermediate, as catalyzed by a first enzyme, and thereby yielding a second intermediate; and isomerizing the second intermediate, as catalyzed by a second enzyme, a third enzyme, or fourth enzyme, and thereby yielding the cannabinoid molecules.

In the method for enhancing titers of the product commencing at the second pathway in the host cell can include: the first intermediate which is geranyl diphosphate and the second intermediate which is cannabigerolic acid.

In the method for enhancing titers of the product commencing at the second pathway in the host cell can include: the first enzyme which is aromatic prenyltransferase; the second enzyme which is tetrahydrocannabiolic acid (THCA) synthase; the third enzyme which is cannabidiolic acid (CBDA) synthase; and the fourth enzyme which is cannabichromenic acid (CBCA) synthase.

In the method for enhancing titers of the product commencing at the second pathway in the host cell can include: the cannabinoid molecules which are THCA, CBDA, and CBCA.

In the method for increasing production of cannabinoid molecules in the host cell can further include: fermenting the host cell; and isolating the cannabinoid molecules.

The present teachings include a family of overexpressed genes to yield polypeptide amino acid sequences among SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. The SEQ ID NO: 1-SEQ ID NO: 12 can include respective amino acid sequences that is at least 95% homologous to the SEQ ID NO: 1-SEQ ID NO: 12. The SEQ ID NO: 1-SEQ ID NO: 12 derive from the family of overexpressed genes inserted into a host cell. The family of overexpressed genes comprises at least nine nodes divided among a plurality of generations in a phylogenetic network and codon-optimized DNA.

The amino sequences among the SEQ ID NO: 1-SEQ ID NO: 12 can derive from *Schizosaccharomyces japonicus, Schizosaccharomyces pombe, Schizosaccharomyces cryophilus, Saccharomyces cerevisiae, Kluyveromyces lactis, Kluyveromyces dobzhanskii, Rhizobium trifolii, Malomonas rubra,* and *Pseudomonas putida*.

The amino acid sequences among the SEQ ID NO: 1-SEQ ID NO: 12 can include: an assembly of amino acids for facilitating malonate transporters and aligned amino acid sequences. A majority of aligned amino acid sequences shared among the SEQ ID NO: 1, the SEQ ID NO: 2, and the SEQ ID NO: 3. A majority of aligned amino acid sequences are shared among the SEQ ID NO: 6 and SEQ ID NO: 7. A majority of aligned amino acid sequences are shared among the SEQ ID NO: 1, the SEQ ID NO: 2, the SEQ ID NO: 3, the SEQ ID NO: 4, the SEQ ID NO: 6, the SEQ ID NO: 7, and the SEQ ID NO: 8. A majority of aligned amino acid sequences are shared among the SEQ ID NO: 1, the SEQ ID NO: 2, the SEQ ID NO: 3, the SEQ ID NO: 4, the SEQ ID NO: 5, the SEQ ID NO: 6, the SEQ ID NO: 7, and the SEQ ID NO: 8. A majority of aligned amino acid sequences are shared among the SEQ ID NO: 9, the SEQ ID NO: 10, the SEQ ID NO: 11, and the SEQ ID NO: 12. A majority of aligned amino acid sequences are shared among the SEQ ID NO: 9 and the SEQ ID NO: 10 along a first subunit. A majority of aligned amino acid sequences are shared among the SEQ ID NO: 11 and the SEQ ID NO: 12, along a second subunit.

The isolated amino acid sequences among the SEQ ID NO: 1-SEQ ID NO: 12 can include the host cell. The host cell can include a pathway commencing at a product, wherein the product is a precursor to cannabinoid molecules.

The present teachings include a modified host organism. The modified host organism can include: at least a first pathway and a second pathway in cells of the modified host organism; and a polypeptide integrated into a plasmid of the cells of the modified host organism. The modified host organism can contain modified genes inserted from at least one of: *Schizosaccharomyces japonicus, Schizosaccharomyces pombe, Schizosaccharomyces cryophilus, Saccharomyces cerevisiae, Kluyveromyces lactis, Kluyveromyces dobzhanskii, Rhizobium trifolii, Malomonas rubra, Pseudomonas putida,* and *Malonomonas rubra*. The first pathway can take carbon flux away from a product in response to the polypeptide integrated into the plasmid of the cells of the modified host organism. The second pathway can provide carbon flux towards the product in response to the polypeptide integrated into the plasmid of the cells of the modified host organism. The polypeptide can include an amino acid sequence selected from: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

DRAWINGS

Those of skill in the art will understand that the drawings, described below, are for illustrative purposes only. The drawings are not intended to limit the scope of the present teachings in any way.

FIG. 1 depicts a table of amino acids used to construct the (amino acid) sequences in proteins.

FIG. 4 depicts sequence alignments and relationships for the malonate transporters herein encoded by a MAE1 gene. FIG. 4 discloses SEQ ID NOS 2, 3 and 1, respectively, in order of appearance.

FIG. 5 depicts sequence alignments and relationships for the malonate transporters herein encoded by a JEN2 gene. FIG. 5 discloses SEQ ID NOS 6-7, respectively, in order of appearance.

FIG. 6 depicts sequence alignments and relationships for the malonate transporters herein encoded by a single polypeptide. FIG. 6 discloses SEQ ID NOS 4, 8, 2-3, 1 and 6-7, respectively, in order of appearance.

Figures 7A, 7B:
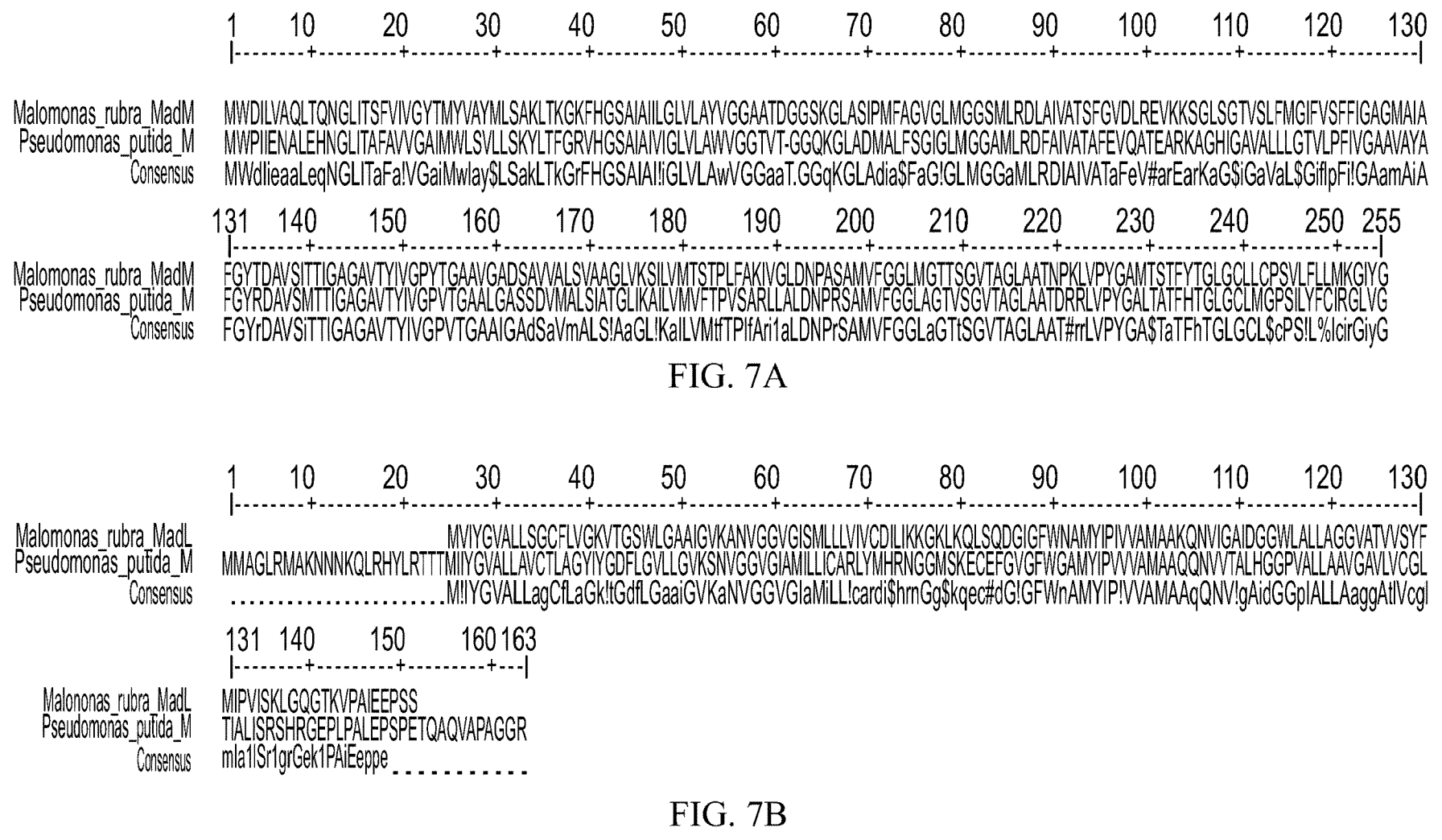

FIGS. 7A-7B depicts sequence alignments and relationships for the malonate transporters herein encoded by multiple polypeptides, where FIG. 7A depicts alignments of M-subunits and FIG. 7B depicts alignments of L-subunits. FIG. 7A discloses SEQ ID NOS 9-10, respectively, in order of appearance. FIG. 7B discloses SEQ ID NOS 11-12, respectively, in order of appearance.

Figure 8:
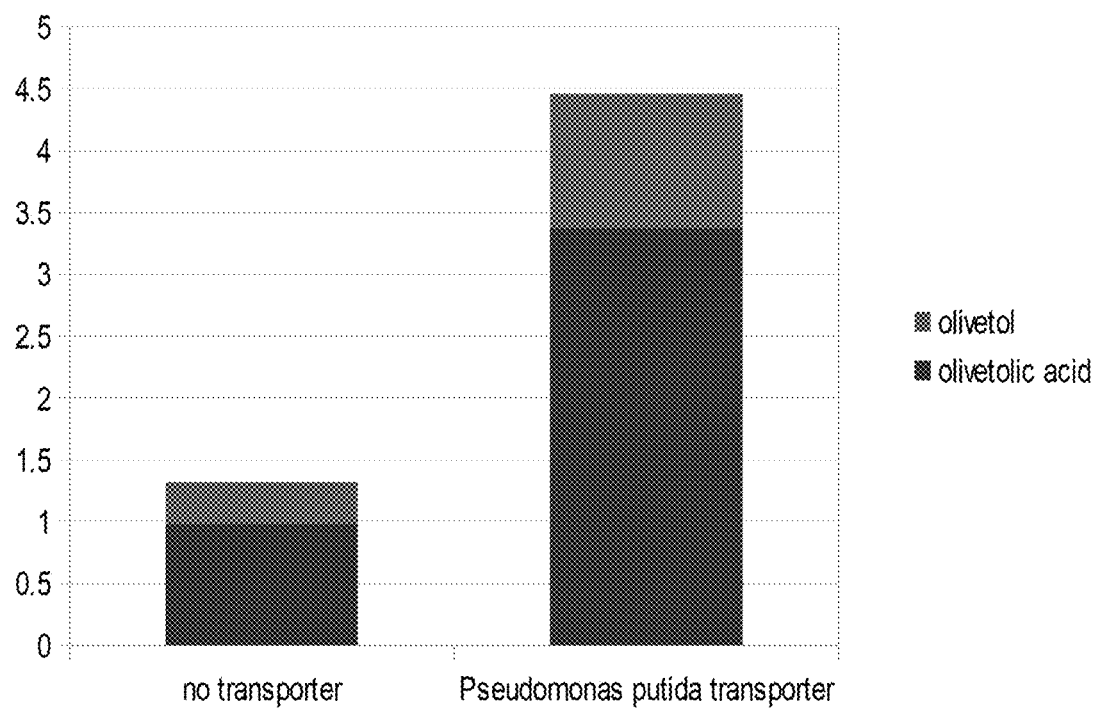

FIG. 8 depicts a fold increase in cannabinoid precursors where the malonate transporters herein are overexpressed.

Figure 9:
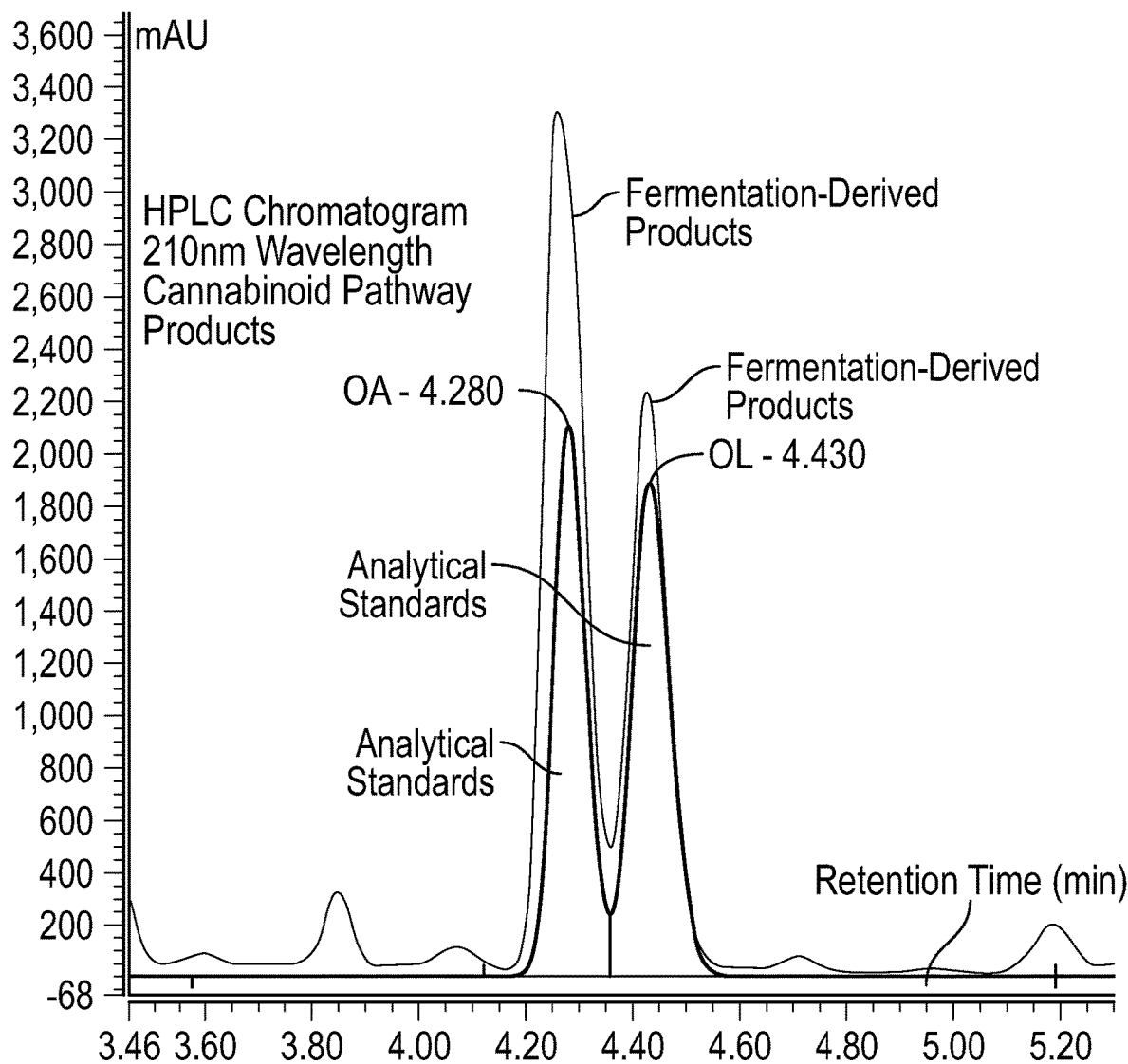

FIG. 9 depicts fermentation products where the malonate transporters herein are overexpressed in a HPLC chromatogram.

Figure 10:
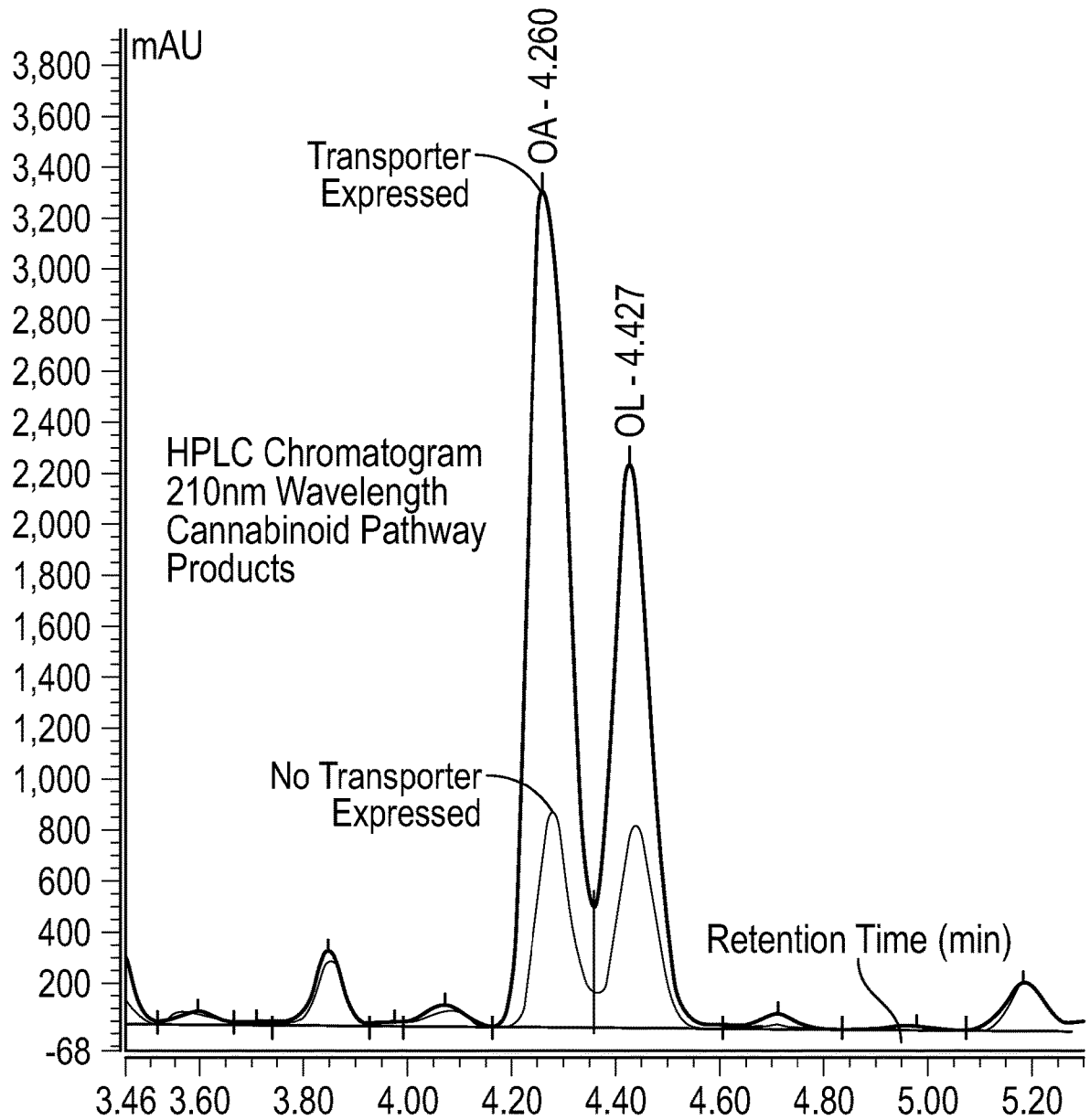

FIG. 10 depicts a HPLC chromatogram of cannabinoid precursors where the malonate transporters are not overexpressed and the malonate transporters herein are overexpressed.

Figure 11:
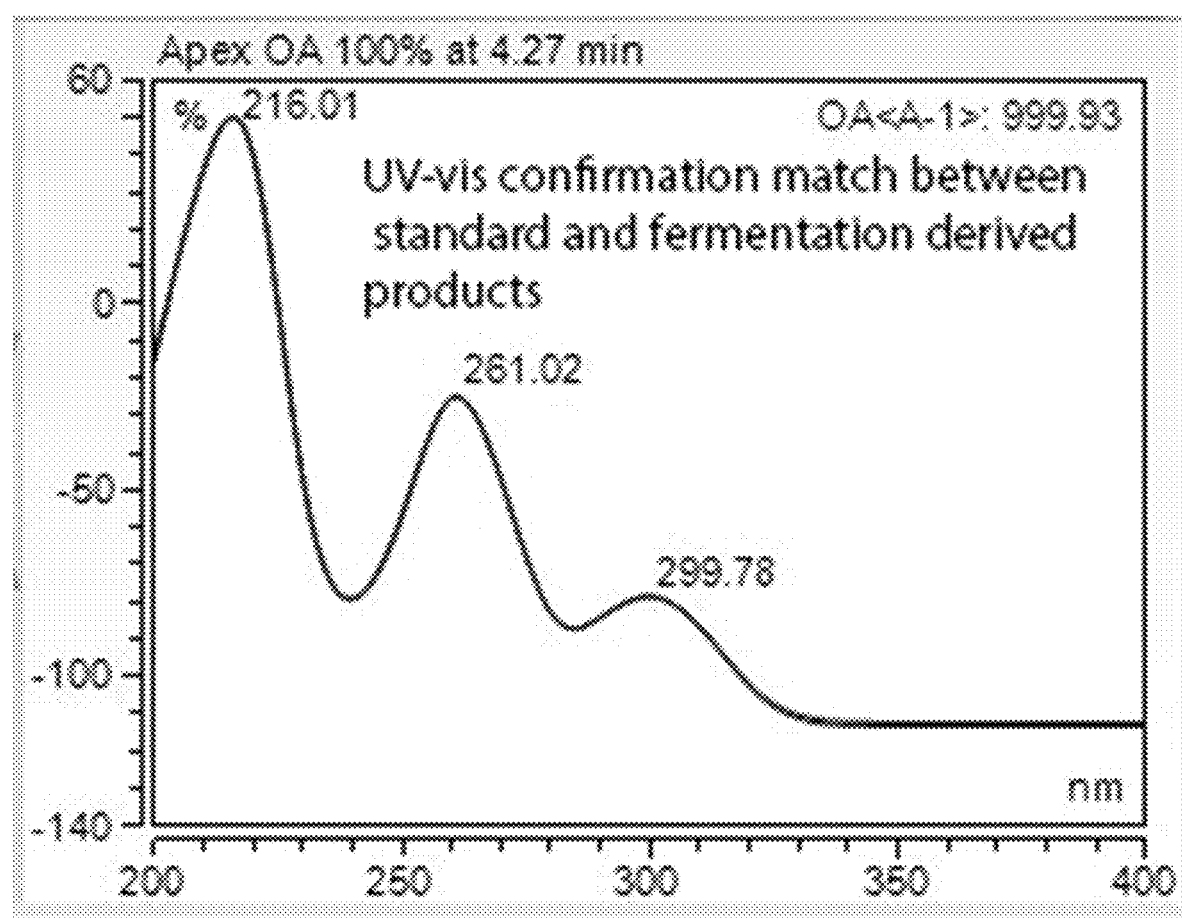

FIG. 11 depicts fermentation products where the malonate transporter therein is overexpressed in an ultraviolet (UV)-visible (vis) spectrum.

DETAILED DESCRIPTION

The present invention generally relates to the production of cannabinoids in a heterologous cell and to methods for improving production of precursor molecules to the cannabinoids by genetically modifying the host organism. More specifically, a method for production of cannabinoids by increasing a concentration of the precursor molecule is disclosed. The methodologies described in this invention are applicable to all cannabinoid and terpene species produced by fermentation that include, but are not limited to: cannabinoids produced by the metabolic pathway commencing with olivetolic acid; cannabinoids produced by the metabolic pathway commencing with divarinic acid; cannabinoids produced by the metabolic pathway commencing with orsellinic acid; and terpenes produced by the metabolic pathway commencing with geranyl diphosphate.

Aspects of the present teachings may be further understood in light of the following figures, which should not be construed as limiting the scope of the present teachings in any way.

FIG. 1 is a table of the amino acid residues found in amino acid sequences. The amino acid sequences are the molecular basis for constructing and assembling proteins, such as enzymes. Genes are regions of deoxyribonucleic acid (DNA). The genetic code defines the sequence of nucleotide triplets (i.e., codons) for specifying which amino acids are added during protein synthesis. The amino acid sequences in the proteins, as defined by the sequence of a gene, are encoded in the genetic code. Peptide bonds (i.e., polypeptides) are formed between amino acids and assemble three-dimensionally (3-D). The 3-D assembly can influence the properties, function, and conformational dynamics of the protein. Within biological systems, the protein may: (i) catalyze reactions as enzymes; (ii) transport vesicles, molecules, and other entities within cells as transporter entities; (iii) provide structure to cells and organisms as protein filaments; (iv) replicate DNA; and (v) coordinate actions of cells as cell signalers.

The system comprises at least one or more enzymes that function to import a precursor molecule for the pathways above into the cell, especially for transporting malonic acid or malonates. These enzymes are malonate transporters that contain one or more polypeptide chains.

Figure 2A:
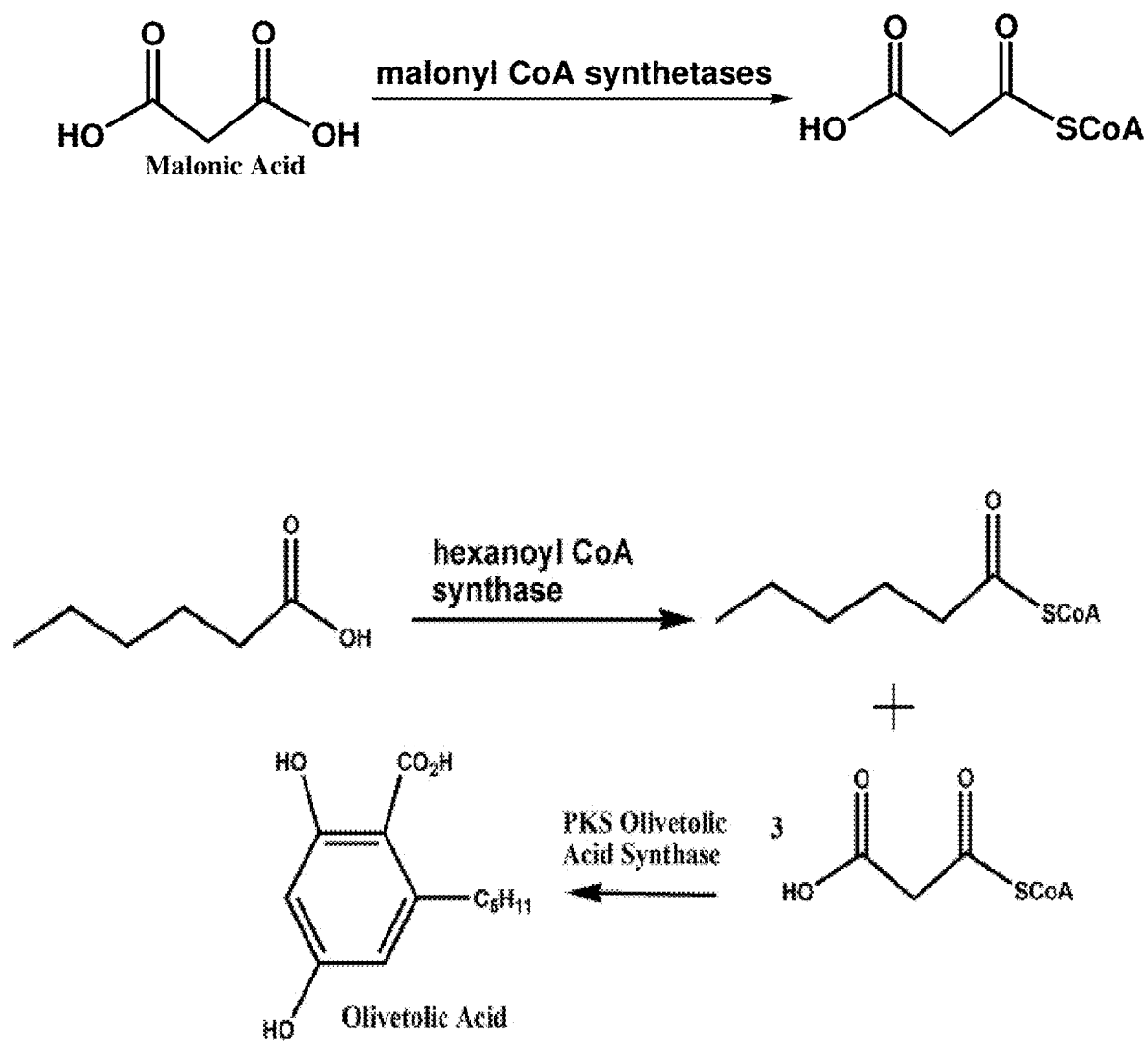
FIG. 2A depicts the pathways involved in the biosynthesis of olivetolic acid.
Figure 2B:
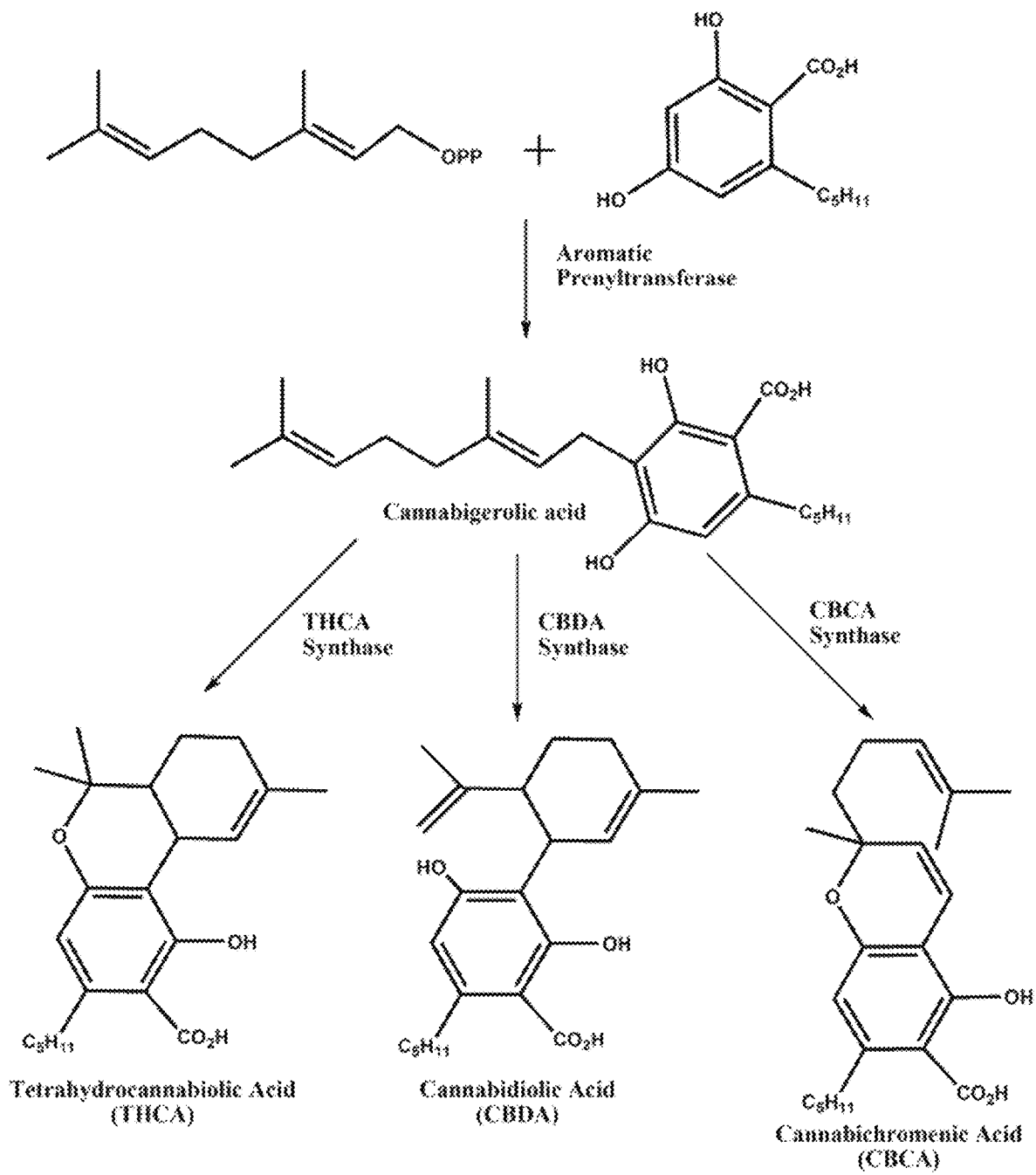
FIG. 2B depicts the pathways involved in the biosynthesis of cannabinoids.

FIG. 2A and FIG. 2B depict biosynthesis pathways impacted by the malonate transporters disclosed herein. Metabolic pathways, biosynthesis pathways, and pathways refer to sequential chemical transformations in a cell or an organism.

In the presence of the malonate transporters herein, malonic acid or malonate may be transported into a host cell to yield malonyl-CoA. Maionic acid may be converted to malonyl-CoA in the presence of malonyl CoA synthase or malonyl CoA synthetases. Malonyl CoA synthases do not use energy from nucleoside triphosphates for the formation of malonyl-CoA. Malonyl CoA synthetases use energy from nucleoside triphosphates for the formation of malonyl-CoA. The malonate transporters herein can increase pool of substrate available to malonyl CoA synthase or malonyl CoA synthetases. Accordingly, the output of malonyl-CoA can increase in the presence of the malonate transporters herein without denaturing of malonyl CoA synthase or malonyl CoA synthetases.

In the presence of the malonate transporters herein, olivetolic acid may be directly obtained when three molecules of malonyl-CoA react with one molecule of hexanoyl-CoA via PKS olivetolic acid synthase-mediated enzymes. The linear pentyl alkyl portion ($C_5H_{11}$) connected to the phenyl ring derives from the hexanoyl-CoA, which has $C_5H_{11}$ connected to the carbonyl of the hexanoyl-CoA. Further, decarboxylation of the carboxylic acid group in olivetolic acid may yield olivetol.

In the presence of the malonate transporters herein, the biosynthesis pathway can proceed towards the formation of cannabigerol and cannabinoid molecules, despite the decarboxylation. In the presence of the malonate transporters herein in the host cells, the geranyl unit from geranyl diphosphate can selectively and exclusively add to the carbon of olivetol that is concomitantly in the ortho-position to both phenol groups of olivetol. In turn, cannabigerol, which is the decarboxylated derivative of cannabigerolic acid, can be obtained. Accordingly, conversion of olivetolic acid to olivetol in the presence of the malonate transporters herein does not revert to malonate-CoA, hexonyl-CoA, or other structures.

In the presence of the malonate transporters herein, olivetolic acid may be indirectly obtained when three molecules of malonyl-CoA react with one molecule of hexanoyl-CoA via a $C_{12}$ polyketide intermediate (not depicted in FIG. 2A). The $C_{12}$ polyketide intermediate has a chemical formula of:

$$(H_{11}C_5-)(C)(=O)(-CH_2-)C(=O)(-CH_2-)(C)(=O)(-CH_2-)(C)(=O)(-SCoA) \qquad (1).$$

In the presence of the malonate transporters herein, decarboxylations of malonyl-CoA yields acetyl-SCoA enolate. Upon a first decarboxylation of the first malonyl-CoA, the resulting acetyl-SCoA enolate is a nucleophile. The nucleophile reacts with hexanoyl-CoA and thereby increases the carbon chain length by two carbons. This structure is an eight carbon long chain containing a single 1,3-dicarbonyl motif. The second and third decarboxylations of the second malonyl-CoA and the third malonyl-CoA react with the eight carbon long structure containing the single 1,3-dicarbonyl motif to yield formula 1.

The conversion of malonate or malonic acid, as transported by malonate transporters herein, to malonyl-CoA may facilitate pathways and carbon fluxes that yield products, such as olivetolic acid or structurally similar aromatic systems. These products may be precursor molecules for yielding intermediate molecules for conversion to cannabinoid target molecules and/or cannabinoid target molecules. In an example, olivetolic acid, as a precursor molecule, may be reacted with geranyl diphospate, as an intermediate molecule, in the presence of aromatic prenyltransferase to yield cannabigerolic acid, as another intermediate molecule. Cannabigerolic acid may then be isomerized to a cannabinoid target molecule. In an example, THCA synthase catalyzes the isomerization for converting cannabigerolic acid to tetrahydrocannabidiolic acid (THCA). In another example, CBDA synthase catalyzes the isomerization for converting cannabigerolic acid to cannabidiolic acid (CBDA). In yet another example, CBCA synthase catalyzes the isomerization for converting cannabigerolic acid to cannabichromenic acid (CBCA).

By expressing or overexpressing malonate transporters, the malonate transporters herein can selectively enrich pathways for forming and transporting malonyl-CoA, without interfering or impeding pathways which yield or commence at: hexanoic acid; malonate; malonic acid; olivetolic acid or olivetol; geranyl diphospate; and/or cannabigerolic acid.

By enriching these pathways, carbon flux is: (i) directed towards these molecules; and (ii) directed away from certain pathways that: (a) consume these molecules by chemical conversion such that (b) the output of cannabigerolic acid or cannabinoid molecules is not decreased. For example, while olivetolic acid or olivetol may be consumed by reacting with geranyl diphosphate to yield cannabigerolic acid (which can be isomerized to a cannabinoid), the malonate transporters herein do not suppress the formation of olivetolic acid or olivetol prior to reacting with geranyl diphosphate. Similarly, the malonate transporters herein do not suppress: (i) the formation of geranyl diphosphate prior to reacting with olivetolic acid; (ii) the formation of hexanoic acid, which is converted to hexanoyl-CoA; and (iii) the formation of hexanoyl-CoA, which reacts with malonyl-CoA to yield olivetolic acid or olivetol. Upon modifying the host cells and expressing the malonate transporter herein, the titers of olivetolic acid or olivetol can experience a fold increase of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.5, 3.6, 3.7, 3.8, 3.9, 4.0, or 4.1.

While not depicted in FIG. 2, the malonate transporters herein are compatible with a pathway commencing at divarinic acid and a metabolic pathway commencing at orsellinic acid to yield cannabinoids.

Figure 3:
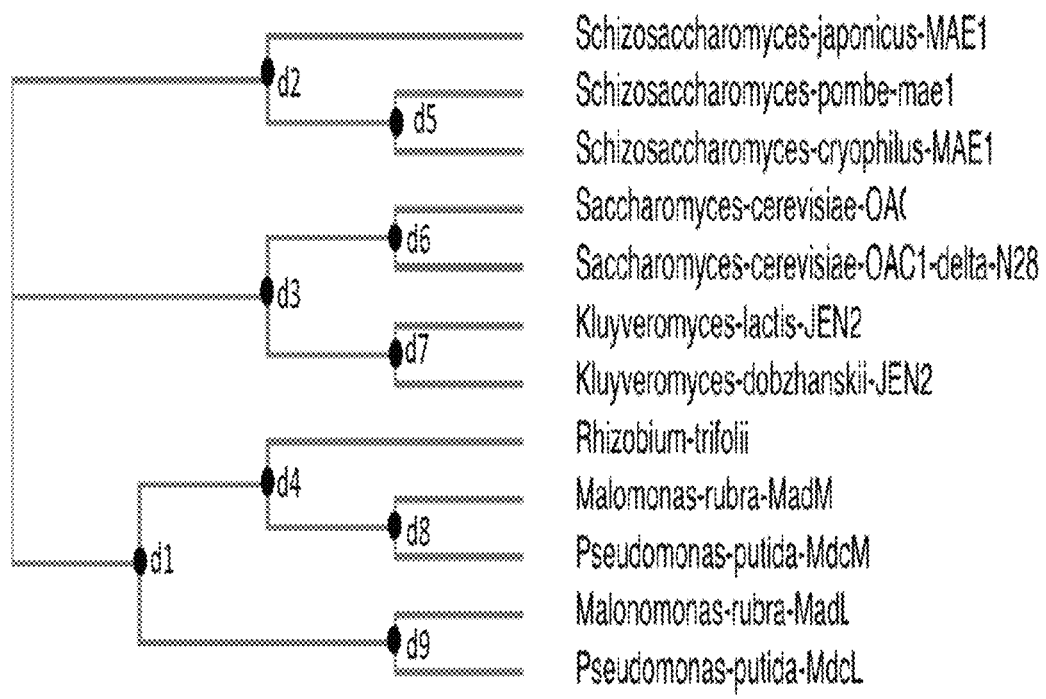
FIG. 3 depicts a phylogenetic network/tree for visualizing the relatedness of malonate transporters herein.

FIG. 3 depicts a phylogenetic network/tree for visualizing the relatedness of malonate transporters herein.

Genes herein may be expressed (or overexpressed) and transformed into strains of the organisms herein to express the malonate transporter herein in the organisms herein. The malonate transporters herein can have shared functions and sequence elements among the individual members of the enzyme family deriving from an expressed gene and a genetically modified organism.

The genes herein can include but are not limited to: MAE1, JEN2, OAC1, OAC1 delta N28, MatC, MadM, MdcM, MadL, and MdcL.

The organisms herein can genetically modified bacteria, fungi, and plants.

The species of the organisms herein, which are genetically modified by inserting the genes herein, can include but are not limited to: *Schizosaccharomyces japonicus*, *Schizosaccharomyces pombe*, *Schizosaccharomyces cryophilus*, *Saccharomyces cerevisiae*, *Kluyveromyces lactis*, *Kluyveromyces dobzhanskii*, and *Rhizobium trifolii*.

The malonate transporters herein can include but are not limited to the combination of species of organisms herein and genes herein: *Schizosaccharomyces japonicus*-MAE1, *Schizosaccharomyces pombe*-MAE1, *Schizosaccharomyces cryophilus*-MAE1, *Saccharomyces cerevisiae*-OAC1, *Saccharomyces cerevisiae*-OAC1 delta N 28, *Kluyveromyces lactis*-JEN2, *Kluyveromyces dobzhanskii*-JEN2, *Rhizobium trifolii*, *Malomonas rubra*-MadM, *Pseudomonas putida*-MdCM, *Malonomonas rubra*-MadL, and *Pseudomonas putida*-MdcL.

In FIG. 3, the phylogenetic network/tree of the malonate transporters herein may have nodes d1, d2, d3, d4, d5, d6, d7, d8, and d9. These nodes are points where a common genetic ancestor may undergo speciation. The point of speciation at node d1 may correspond to a first generation. The points of speciation at nodes d2, d3, and d4 may correspond to a second generation. The points of speciation at nodes d5, d6, d7, d8, and d9 may correspond to a third generation.

At node d2, speciation can lead to malonate transporter *Schizosaccharomyces japonicus*-MAE1 and branching to node d5.

At node d5, speciation can lead to malonate transporters *Schizosaccharomyces pombe*-MAE1 and *Schizosaccharomyces cryophilus*-MAE1.

At node d6, speciation can lead to malonate transporters *Saccharomyces cerevisiae*-OAC1 and *Saccharomyces cerevisiae*-OAC1 delta N28. The sequence of *Saccharomyces cerevisiae*-OAC1 delta N28 is truncated by 28 amino acids, in comparison to *Saccharomyces cerevisiae*-OAC1.

At node d7, speciation can lead to *Kluyveromyces lactis*-JEN2 and *Kluyveromyces* dobzhanskii-JEN2.

At node d4, speciation can lead to *Rhizobium trifolii*-MatC and branching at node d8.

At node d8, speciation can lead to *Malomonas rubra*-MadM and *Pseudomonas putida*-MdCM.

At node d9, speciation can lead to *Malonomonas rubra*-MadL and *Pseudomonas putida*-MdcL.

Native DNA sequences may be used or DNA sequences may be codon optimized to improve gene expression and encoding the malonate transporters herein. Sequence alignments of the malonate transporters herein may be determined to identify regions of similarity resulting from functional, structural, or evolutionary relationships between the amino acid sequences of the malonate transporters herein.

In an example, the MadL and MadM genes from *Malomonas rubra* are co-overexpressed in 1:1 stoichiometry to facilitate transport of malonic acid or its salt, malonate, into the host cell for incorporation and eventual conversion into cannabinoid molecules.

In an example, the MatC gene from *Rhizobium trifolii* is overexpressed to facilitate transport of malonic acid or its salt, malonate, into the host cell for incorporation and eventual conversion into cannabinoid molecules.

In an example, the OAC1 gene from *Saccharomyces cerevisiae* is overexpressed to facilitate transport of malonic acid or its salt, malonate, into the host cell for incorporation and eventual conversion into cannabinoid molecules. Either full length OAC1 may be used or an N-terminal truncation can be used to change the subcellular localization of the enzyme.

In an example, the MAE1 gene from *Schizosacaaharomyces pombe* is overexpressed to facilitate transport of malonic acid or its salt, malonate, into the host cell for incorporation and eventual conversion into cannabinoid molecules.

In an example, the JEN2 gene from *Kluyveromyces lactis* is overexpressed to facilitate transport of malonic acid or its salt, malonate, into the host cell for incorporation and eventual conversion into cannabinoid molecules.

In an example, the MAE1 gene from *Schizosaccharomyce cryophilus* is overexpressed to facilitate transport of malonic acid or its salt, malonate, into the host cell for incorporation and eventual conversion into cannabinoid molecules.

In an example, the MAE1 gene from *Schizosaccharomyces japonicus* is overexpressed to facilitate transport of malonic acid or its salt, malonate, into the host cell for incorporation and eventual conversion into cannabinoid molecules.

In an example, the JEN2 gene from *Kluyveromyces dobzhanskii* is overexpressed to facilitate transport of malonic acid or its salt, malonate, into the host cell for incorporation and eventual conversion into cannabinoid molecules.

In an example, the MdcL and MdcM genes from *Pseudomonas putida* are co-overexpressed in 1:1 stoichiometry to facilitate transport of malonic acid or its salt, malonate, into the host cell for incorporation and eventual conversion into cannabinoid molecules.

The malonate transporters herein may be single polypeptide enzymes encoded by the MAE1 gene or the JEN2 gene Amino acid sequences of MAE1 or JEN2-derived malonate transporters herein may be obtained from different organisms yet share common amino acid sequence elements (see FIG. 4 and FIG. 5). In FIG. 4, the alignment of *Schizosaccharomyces japonicus*-MAE1, *Schizosaccharomyces pombe*-MAE1, and *Schizosaccharomyces cryophilus*-MAE1 are depicted. In FIG. 5, the alignment of *Kluyveromyces lactis*-JEN2 and *Kluyveromyces* dobzhanskii-JEN2 are depicted.

Figure 6:
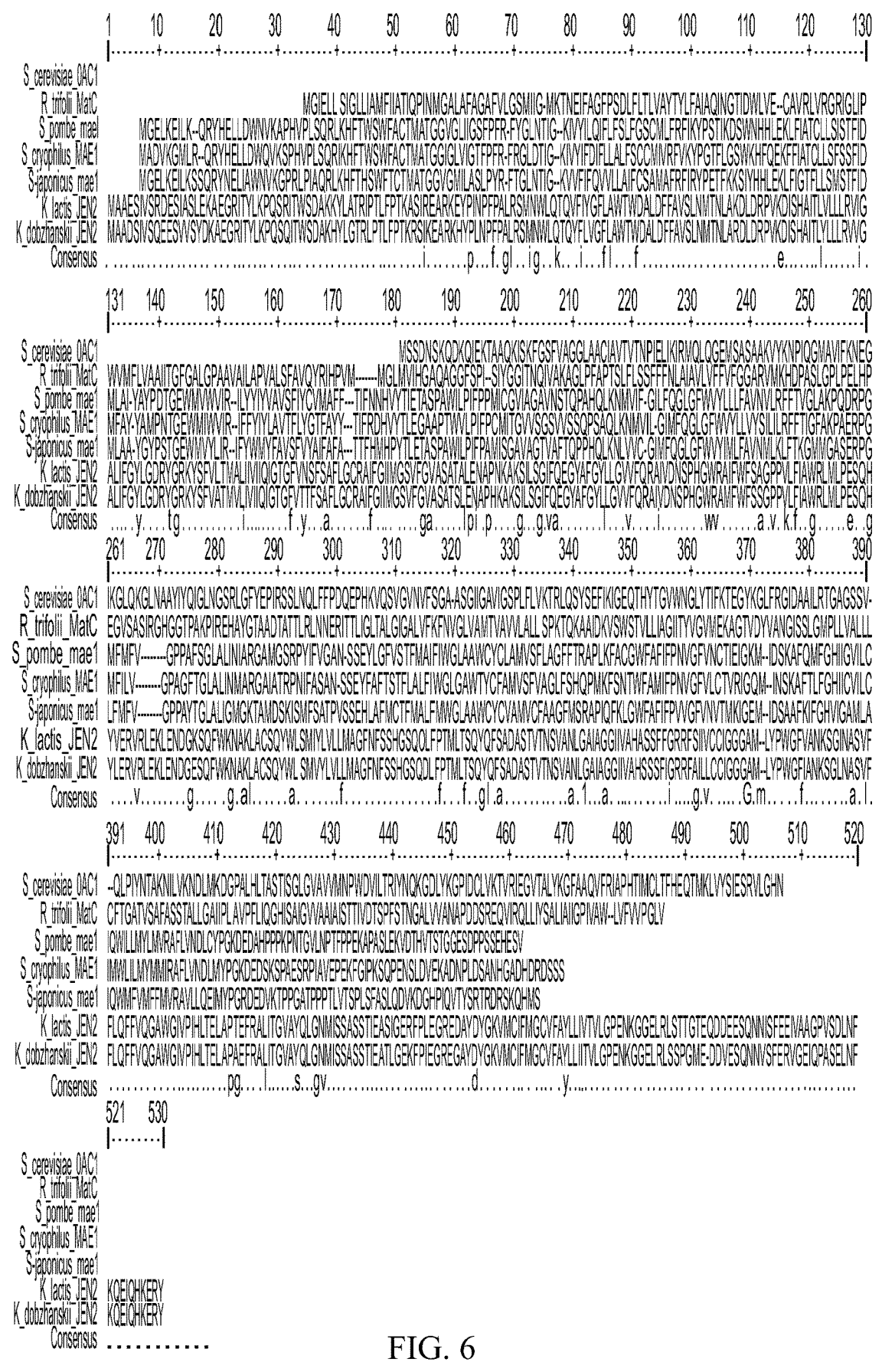

Amino acid sequence elements may share common amino acid sequence elements to malonate transporters herein encoded by a single polypeptide (see FIG. 6). In FIG. 6, the alignment of *Schizosaccharomyces japonicus*-MAE1, *Schizosaccharomyces pombe*-MAE1, *Schizosaccharomyces cryophilus*-MAE1, *Saccharomyces cerevisiae*-OAC1 delta N, *Kluyveromyces lactis*-JEN2, *Kluyveromyces* dobzhanskii-JEN2, and *Rhizobium trifolii*-MatC are depicted.

Malonate transporters herein comprising multiple polypeptides may be encoded by the MadM, MadL MdcM, or MdcL genes; and share amino acid sequence elements which have: (i) an alignment of M-subunit(s) (see FIG. 7A); and (ii) an alignment of L-subunit(s) (see FIG. 7B). In FIG. 7A, the alignment of *Malomonas rubra*-MadM and *Pseudomonas putida*-MdCM are depicted. In FIG. 7B, the alignment of *Malonomonas rubra*-MadL and *Pseudomonas rubra*-MdcL are depicted.

EXAMPLES

Aspects of the present teachings may be further understood in light of the following examples, which should not be construed as limiting the scope of the present teachings in any way.

In the examples below, genetically engineered host cells may be any species of yeast herein, including but not limited to any species of *Saccharomyes, Candida, Schizosaccharomyces, Yarrowia*, etc., which have been genetically altered to produce precursor molecules, intermediate molecules, and cannabinoid molecules. Additionally, genetically engineered host cells may be any species of filamentous fungus, including but not limited to any species of *Aspergillus*, which have been genetically altered to produce precursor molecules, intermediate molecules, and cannabinoid molecules.

In the examples below, the malonate transporters herein derive from bacteria herein, such as *Rhizobium trifolii, Malomonas rubra*, and *Pseudomonas putida*. Genes from the bacteria herein are inserted into the yeast herein or filamentous fungus. Fermentation; production of cannabinoid molecules; production of intermediate molecules; and production of precursor molecules occur in yeast and other types of fungi.

The combination of the malonate transporters herein deriving from the bacteria herein and the yeast herein or filamentous fungus as host cells increase the titers of precursor molecules, intermediate molecules, and cannabinoid molecules. Stated another way, the amounts of precursor molecules, intermediate molecules, and cannabinoids molecules can be increased in the host cells on the fold scale by merely incorporating malonate transporters herein. The malonate transporters herein are introduced in the host cells such that the level of the malonate transporters in the host cell is increased in comparison to the natural level of malonate transporters in the host cells. The incorporation of the malonate transporters herein does not damage the host cells. Instead, the malonate transporters herein incorporated into the host cell direct the carbon flux in the host cells towards precursor molecules, intermediate molecules, and cannabinoids molecules. As described in more detail in the examples below, the carbon flux towards cannabinoids in the host cells is increased from the increased pool of malonate.

Example 1—A Protocol for Facilitating Malonate Transport

Gene sequences are chosen from publicly available databases. The gene sequences are codon optimized to improve expression using techniques disclosed in U.S. patent application Ser. No. 15/719,430, filed Sep. 28, 2017, entitled "An Isolated Codon Optimized Nucleic Acid". DNA sequences are synthesized and cloned using techniques known in the art. Gene expression is controlled by inducible promoter systems. Malonate transporter genes are transformed into strains of an organism using standard yeast or fungus transformation methods. The organism contains cells, wherein the cells contain expressed malonate transporter genes for: (i) producing cannabinoid molecules and precursor molecules to cannabinoid molecules; and (ii) increasing an output of cannabinoid molecules and precursor molecules to cannabinoid molecules. In the presence or absence of exogenous malonic acid or malonate, fermentations are run to determine if the importers, such as the malonate transporters herein, are able to import malonate into the cell for incorporation and eventual conversion into cannabinoid molecules. The malonate transporters herein can be integrated into the genome of the cell or maintained as an episomal plasmid. Samples are: (i) extracted using a combination of dissolution, purification, and fermentation steps; and (ii) analyzed by HPLC for the presence of precursor molecules, intermediate molecules, and cannabinoid molecules.

More specifically, the samples are extracted with the aid of solid phase materials (e.g., functional polymeric resins) to selectively adsorb products (e.g., olivetolic acid and olivetol) from the fermentation broth. The unwanted products are removed from these adsorbing materials via washing; filtration; centrifugation; or floatation and decanting. The desired products are: (i) eluted from the adsorbing materials using solvents, such as acetonitrile, methanol, ethanol, or isopropyl alcohol; and (ii) purified. The adsorbing materials are returned to the position in the process cycle where adsorption of products from the fermentation onto the adsorption materials occurs. Water:methanol and water:ethanol mixtures can be used to remove unwanted materials while keeping the desired product (e.g., olivetolic acid and olivetol) adsorbed in the functional polymeric resins, wherein the mixtures are 0-70% methanol or ethanol. These steps may be used in different combinations best suited for the optimization requirements of particular fermentation products.

Example 2—A Fold Increase in Cannabinoid Precursors where the Malonate Transporters Herein are Overexpressed Cannabinoids and precursors to the cannabinoids are made in yeast or fungus using malonate transporters herein from *Pseudomonas*. Titers of olivetol and olivetolic acid where malonate transporters herein are expressed or overexpressed and not expressed are compared (see FIG. 8). In FIG. 8, the scale is in level units which correspond to titers of olivetol or olivetolic acid. Responsive to expressing malonate transporters herein from *Pseudomonas putida*, the titers of olivetol and olivetolic acid are increased on the fold scale. When malonate transporters herein from *Pseudomonas putida* are not expressed, the titers of olivetolic acid and olivetol correspond to 0.93 level units and 0.42 level units, respectively. At these level units, the titers of olivetolic acid and olivetol are too low for practical commercial scale isolation of olivetolic acid and olivetol from non-genetically modified or altered strains. When malonate transporters herein from *Pseudomonas putida* are expressed, the titers of olivetolic acid and olivetol correspond to 3.45 level units and 1.08 level units, respectively. Accordingly, the expression of the malonate transporters herein from *Pseudomonas putida* leads to 3.70 fold increase in the amount of olivetolic acid and 2.57 fold increase in olivetol. At these level units, the titers of olivetolic acid and olivetol are multiple folds higher and thus, more amenable for practical commercial scale isolations than olivetolic acid and olivetol from non-genetically modified or non-altered strains.

Example 3—Fermentation Products where the Malonate Transporters Herein are Overexpressed in a HPLC Chromatogram Spectra are compared to analytical standards to confirm the presence of cannabinoid compounds upon fermentation of organisms, where malonate transporters herein are expressed (see FIG. 9). In FIG. 9, OA corresponds to olivetolic acid and OL corresponds to olivetol. The analytical standards for OA and OL exhibit maximum absorption at a wavelength of 210 nanometers (nm) and retention times of 4.280 minutes and 4.430 minutes, respectively. Malonate transporters herein are expressed or overexpressed in the organisms herein and thereby increase the titers of OA and OL in the organisms above. The organisms herein are fermented for isolating chemical products. In FIG. 9, the HPLC chromatograms of the isolated products are taken at a wavelength of 210 nm and the peaks exhibited are identical to the analytical standards for OA and OL. This indicates that fermentation can isolate OA and OL as products of interest (i.e., precursor molecules to cannabinoids), which can be used to yield and obtain: (i) intermediate molecules, which can be further functionalized to cannabinoid molecules; and (ii) cannabinoid molecules. The malonate transporters herein do not interfere with the formation and isolation of the intermediate molecules and cannabinoids molecules. More specifically, the malonate transporters herein do not interact, alter, or denature: malonyl CoA synthase, malonyl CoA synthetases, hexanoyl CoA, PKS olivetolic acid synthase, PKS olivetol synthase, aromatic prenyltransferase, tetrahydrocannabiolic acid (THCA) synthase, cannabidiolic acid (CBDA) synthase, or cannabichromenic acid (CBCA) synthase.

Example 4—HPLC Chromatogram of Cannabinoid Precursors where the Malonate Transporters Herein are not Overexpressed and the Malonate Transporters Herein are Overexpressed Spectra from malonate transporters herein expressed in strains are compared to negative controls where malonate transporters herein not expressed in strains to measure the presence and production of chemical products facilitated by malonate transporters herein (see FIG. 10). In FIG. 10, OA corresponds to olivetolic acid and OL corresponds to olivetol. HPLC chromatograms and absorption at a wavelength of 210 nm are taken for: (i) a set of samples derived from organisms where the malonate transporters herein are not expressed; and (ii) a set of samples derived from organisms where the malonate transporters herein are expressed. Where malonate transporters are not expressed, a peak corresponds to OA which has an absorbance of 870 mAU at a retention time of 4.260 minutes; and a peak corresponds to OL which has an absorbance of 800 mAU at a retention time of 4.427 minutes. Where the malonate transporters herein are expressed, a peak corresponds to OA which has an absorbance of 3300 mAU at a retention time of 4.260 minutes; and a peak corresponds to OL which has an absorbance of 2250 mAU at a retention time of 4.427 minutes. The absorbance is proportional to concentration or titers. For the HPLC and absorption analysis, the weight and volume are identical for the set of samples containing organisms where the malonate transporters herein are not expressed and the set of samples where the malonate transporters herein are expressed. Stated another way, the difference between the two set of samples results the expression of the malonate transporters herein. The absorbance of OA and OL where the malonate transporters herein are expressed is 3.79 times and 2.55 times greater than where the malonate transporters herein are not expressed, respectively. Accordingly, this indicates that the titers of OA and OL are enhanced by a fold of 3.79 and 2.55 where the malonate transporters herein are expressed.

Example 5—Fermentation Products where the Malonate Transporter Therein are Overexpressed in an Ultraviolet (UV)-Visible (Vis) Spectrum UV-Vis spectroscopy is used to match standards to fermentation products (see FIG. 11). A set of samples containing the fermentation derived products are compared to a set of samples containing analytical standards for olivetolic acid and olivetol. Organisms herein are genetically modified and fermented, where malonate transporters herein are expressed (see FIG. 9). The extraction and purification steps, as described in Example 1, are subsequently performed to selectively isolate the fermentation derived products in the set of samples. The measured weight of the fermentation derived products is identical to the measured weight of the analytical standards. The measured volume of solvent for dissolving the fermentation derived products is identical to the measured volume for dissolving the analytical standards. Both set of samples are dissolved in the same solvent, such as methanol. Other organic solvents can be used. The concentrations of both set of samples are identical to each other in terms of weight per volume. The optical absorbance of both sets of samples is identical to each other, as the set of samples containing the fermentation derived products is directly over the set of samples containing the analytical standards. The peaks of maximum of optical absorbance for the set of samples containing the fermentation derived products absorb at the same wavelengths as the set of samples containing the analytical standards. The optical absorbance and wavelengths of maximum absorbance (216.01 nm, 261.02 nm, and 299.78 nm) indicates that the fermentation derived products are olivetolic acid and olivetol. Further, this also indicates that expressing malonate transporters herein and fermentation of the genetically modified organisms herein leads to the isolation of olivetolic acid and olivetol.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A genetically modified microbial cell comprising at least one polypeptide that is non-naturally occurring in the cell and that allows for production of a terpene in the genetically modified microbial cell, and at least one malonate transporter gene that is non-naturally occurring in the cell, wherein the non-naturally occurring polypeptide comprises at least one enzyme selected from the group consisting of aromatic prenyltransferase (CBGAS), tetrahydrocannabiolicacid (THCA) synthase, cannabidiolic acid (CBDA) synthase, cannabichromenic acid (CBCA) synthase, aromatic prenyltransferase, malonyl CoA synthase, PKS olivetolic acid synthase and PKS olivetol synthase.

2. The cell of claim 1, wherein the terpene is a cannabinoid molecule or cannabinoid precursor molecule.

3. The cell of claim 1, wherein the malonate transporter gene is expressed, causing an increase in the level of malonic acid or malonate in the cell.

4. The cell of claim 1, wherein the malonate transporter is naturally occurring in a *Schizosaccharomyces japonicus, Schizosaccharomyces pombe, Schizosaccharomyces cryophilus, Saccharomyces cerevisiae, Kluyveromyces lactis, Kluyveromyces dobzhanskii, Rhizobium trifolii, Malomonas rubra, Pseudomonas putida*, or *Malonomonas rubra*.

5. The cell of claim 1, wherein the malonate transporter comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12.

6. The cell of claim 1, which is a filamentous fungus or a yeast.

7. The cell of claim 1, which is a yeast in the genus *Saccharomyces, Candida, Schizosaccharomyces* or *Yarrowia*.

8. The cell of claim 1, which is a *Schizosaccharomyces japonicus, Schizosaccharomyces pombe, Schizosaccharomyces cryophilus, Saccharomyces cerevisiae, Kluyveromyces lactis, Kluyveromyces* dobzhanskii or *Rhizobium trifolii*.

9. The cell of claim 1, which produces the cannabinoid molecule THCA, cannabigerolic acid, CBDA, CBCA or any combination thereof.

10. The cell of claim 1, further comprising a second malonate transporter gene that is not naturally occurring in the cell.

11. The cell of claim 1, wherein the at least one malonate transporter gene is integrated into the genome of the cell.

12. The cell of claim 1, wherein the at least one malonate transporter gene is maintained in the cell as an episomal plasmid.

13. The cell of claim 1, which produces the cannabinoid precursor molecule olivetol, olivetolic acid, a derivative of olivetol, a derivative of olivetolic acid, or any combination thereof.

* * * * *

SEQUENCE LISTING

```
<160> NUMBER OF SEQ ID NOS: 12

<210> SEQ ID NO 1
<211> LENGTH: 441
<212> TYPE: PRT
<213> ORGANISM: Schizosaccharomyces japonicus

<400> SEQUENCE: 1

Met Gly Glu Leu Lys Glu Ile Leu Lys Ser Ser Gln Arg Tyr Asn Glu
1               5                   10                  15

Leu Ile Ala Trp Asn Val Lys Gly Pro Arg Leu Pro Ile Ala Gln Arg
            20                  25                  30

Leu Lys His Phe Thr Trp Ser Trp Phe Thr Cys Thr Met Ala Thr Gly
        35                  40                  45

Gly Val Gly Met Ile Leu Ala Ser Leu Pro Tyr Arg Phe Thr Gly Leu
    50                  55                  60

Asn Thr Ile Gly Lys Val Val Phe Ile Phe Gln Val Val Leu Leu Ala
65                  70                  75                  80

Ile Phe Cys Ser Ala Met Ala Phe Arg Phe Ile Arg Tyr Pro Glu Thr
                85                  90                  95

Phe Lys Lys Ser Ile Tyr His His Leu Glu Lys Leu Phe Ile Gly Thr
            100                 105                 110

Phe Leu Leu Ser Met Ser Thr Phe Ile Asp Met Leu Ala Ala Tyr Gly
        115                 120                 125

Tyr Pro Ser Thr Gly Glu Trp Met Val Tyr Leu Ile Arg Ile Phe Tyr
    130                 135                 140

Trp Met Tyr Phe Ala Val Ser Phe Val Tyr Ala Ile Phe Ala Phe Ala
145                 150                 155                 160

Thr Thr Phe His Met His Pro Tyr Thr Leu Glu Thr Ala Ser Pro Ala
                165                 170                 175

Trp Ile Leu Pro Ile Phe Pro Ala Met Ile Ser Gly Ala Val Ala Gly
            180                 185                 190

Thr Val Ala Phe Thr Gln Pro Pro His Gln Leu Lys Asn Leu Val Val
        195                 200                 205

Cys Gly Ile Met Phe Gln Gly Leu Gly Phe Trp Val Tyr Ile Met Leu
    210                 215                 220

Phe Ala Val Asn Met Leu Lys Leu Phe Lys Gly Met Met Gly Ala
225                 230                 235                 240
```

```
Ser Glu Tyr Arg Pro Gly Leu Phe Met Phe Val Gly Pro Pro Ala Tyr
            245                 250                 255

Thr Gly Leu Ala Leu Ile Gly Met Gly Lys Thr Ala Met Asp Ser Lys
        260                 265                 270

Ile Ser Met Phe Ser Ala Thr Pro Val Ser Ser Glu His Leu Ala Phe
        275                 280                 285

Met Cys Thr Phe Met Ala Leu Phe Met Trp Gly Leu Ala Ala Trp Cys
        290                 295                 300

Tyr Cys Val Ala Met Val Cys Phe Ala Ala Gly Phe Met Ser Arg Ala
305                 310                 315                 320

Pro Ile Gln Phe Lys Leu Gly Trp Phe Ala Phe Ile Phe Pro Val Val
                325                 330                 335

Gly Phe Val Asn Val Thr Met Lys Ile Gly Glu Met Ile Asp Ser Ala
                340                 345                 350

Ala Phe Lys Ile Phe Gly His Val Ile Gly Ala Met Leu Ala Ile Gln
                355                 360                 365

Trp Met Phe Val Met Phe Phe Met Val Arg Ala Val Leu Leu Gln Glu
                370                 375                 380

Ile Met Tyr Pro Gly Arg Asp Glu Asp Val Lys Thr Pro Pro Gly Ala
385                 390                 395                 400

Thr Pro Pro Pro Thr Leu Val Thr Ser Pro Leu Ser Phe Ala Ser Leu
                405                 410                 415

Gln Asp Val Lys Asp Gly His Pro Ile Gln Val Thr Val Ser Arg Thr
                420                 425                 430

Arg Asp Arg Ser Lys Gln His Met Ser
435                 440

<210> SEQ ID NO 2
<211> LENGTH: 438
<212> TYPE: PRT
<213> ORGANISM: Schizosaccharomyces pombe

<400> SEQUENCE: 2

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
                20                  25                  30

His Phe Thr Trp Ser Trp Phe Ala Cys Thr Met Ala Thr Gly Gly Val
            35                  40                  45

Gly Leu Ile Ile Gly Ser Phe Pro Phe Arg Phe Tyr Gly Leu Asn Thr
        50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
                100                 105                 110

Leu Ser Ile Ser Thr Phe Ile Asp Met Leu Ala Ile Tyr Ala Tyr Pro
            115                 120                 125

Asp Thr Gly Glu Trp Met Val Trp Val Ile Arg Ile Leu Tyr Tyr Ile
        130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175
```

```
Leu Pro Ile Phe Pro Pro Met Ile Cys Gly Val Ile Ala Gly Ala Val
                180                 185                 190

Asn Ser Thr Gln Pro Ala His Gln Leu Lys Asn Met Val Ile Phe Gly
            195                 200                 205

Ile Leu Phe Gln Gly Leu Gly Phe Trp Val Tyr Leu Leu Leu Phe Ala
        210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435

<210> SEQ ID NO 3
<211> LENGTH: 441
<212> TYPE: PRT
<213> ORGANISM: Schizosaccharomyces cryophilus

<400> SEQUENCE: 3

Met Ala Asp Val Lys Gly Met Leu Arg Gln Arg Tyr His Glu Leu Leu
1               5                   10                  15

Asp Trp Gln Val Lys Ser Pro His Val Pro Leu Ser Gln Arg Ile Lys
                20                  25                  30

His Phe Thr Trp Ser Trp Phe Ala Cys Thr Met Ala Thr Gly Gly Ile
            35                  40                  45

Gly Leu Val Ile Gly Thr Phe Pro Phe Arg Phe Arg Gly Leu Asp Thr
        50                  55                  60

Ile Gly Lys Ile Val Tyr Ile Phe Asp Ile Phe Leu Leu Ala Leu Phe
65                  70                  75                  80

Ser Cys Cys Met Ile Val Arg Phe Val Lys Tyr Pro Gly Thr Phe Leu
                85                  90                  95

Gly Ser Trp Lys His Phe Gln Glu Lys Phe Phe Ile Ala Thr Cys Leu
```

```
                    100                 105                 110
Leu Ser Phe Ser Ser Phe Ile Asp Met Phe Ala Val Tyr Ala Met Pro
            115                 120                 125

Asn Thr Gly Glu Trp Met Ile Trp Val Ile Arg Ile Phe Phe Tyr Ile
        130                 135                 140

Tyr Leu Ala Val Thr Phe Leu Tyr Gly Thr Phe Ala Tyr Thr Ile
145                 150                 155                 160

Phe Arg Asp His Val Tyr Thr Leu Gly Ala Ala Pro Thr Trp Val
            165                 170                 175

Leu Pro Ile Phe Pro Cys Met Ile Thr Gly Val Val Ser Gly Ser Val
            180                 185                 190

Val Ser Ser Gln Pro Ser Ala Gln Leu Lys Asn Met Val Ile Leu Gly
            195                 200                 205

Ile Met Phe Gln Gly Leu Gly Phe Trp Val Tyr Leu Leu Val Tyr Ser
        210                 215                 220

Ile Leu Ile Leu Arg Phe Phe Thr Ile Gly Phe Ala Lys Pro Ala Glu
225                 230                 235                 240

Arg Pro Gly Met Phe Ile Leu Val Gly Pro Ala Gly Phe Thr Gly Leu
                245                 250                 255

Ala Leu Ile Asn Met Ala Arg Gly Ala Ile Ala Thr Arg Pro Asn Ile
            260                 265                 270

Phe Ala Ser Ala Asn Ser Ser Glu Tyr Phe Ala Phe Thr Ser Thr Phe
        275                 280                 285

Leu Ala Leu Phe Ile Trp Gly Leu Gly Ala Trp Thr Tyr Cys Phe Ala
        290                 295                 300

Met Val Ser Phe Val Ala Gly Leu Phe Ser His Gln Pro Met Lys Phe
305                 310                 315                 320

Ser Asn Thr Trp Phe Ala Met Ile Phe Pro Asn Val Gly Phe Val Leu
                325                 330                 335

Cys Thr Val Arg Ile Gly Gln Met Ile Asn Ser Lys Ala Phe Thr Leu
                340                 345                 350

Phe Gly His Ile Ile Cys Val Ile Leu Cys Ile Met Trp Leu Ile Leu
        355                 360                 365

Met Tyr Met Met Ile Arg Ala Phe Leu Val Asn Asp Leu Met Tyr Pro
        370                 375                 380

Gly Lys Asp Glu Asp Ser Lys Ser Pro Ala Glu Ser Arg Pro Ile Ala
385                 390                 395                 400

Val Glu Pro Glu Lys Phe Gly Ile Pro Lys Ser Gln Pro Glu Asn Ser
                405                 410                 415

Leu Asp Val Glu Lys Ala Asp Asn Pro Leu Asp Ser Ala Asn His Gly
            420                 425                 430

Ala Asp His Asp Arg Asp Ser Ser
            435                 440

<210> SEQ ID NO 4
<211> LENGTH: 324
<212> TYPE: PRT
<213> ORGANISM: Saccharomyces cerevisiae

<400> SEQUENCE: 4

Met Ser Ser Asp Asn Ser Lys Gln Asp Lys Gln Ile Glu Lys Thr Ala
1               5                   10                  15

Ala Gln Lys Ile Ser Lys Phe Gly Ser Phe Val Ala Gly Gly Leu Ala
            20                  25                  30
```

Ala Cys Ile Ala Val Thr Val Thr Asn Pro Ile Glu Leu Ile Lys Ile
            35                  40                  45

Arg Met Gln Leu Gln Gly Glu Met Ser Ala Ser Ala Lys Val Tyr
 50                  55                  60

Lys Asn Pro Ile Gln Gly Met Ala Val Ile Phe Lys Asn Glu Gly Ile
 65                  70                  75                  80

Lys Gly Leu Gln Lys Gly Leu Asn Ala Ala Tyr Ile Tyr Gln Ile Gly
                85                  90                  95

Leu Asn Gly Ser Arg Leu Gly Phe Tyr Glu Pro Ile Arg Ser Ser Leu
            100                 105                 110

Asn Gln Leu Phe Phe Pro Asp Gln Glu Pro His Lys Val Gln Ser Val
            115                 120                 125

Gly Val Asn Val Phe Ser Gly Ala Ala Ser Gly Ile Ile Gly Ala Val
            130                 135                 140

Ile Gly Ser Pro Leu Phe Leu Val Lys Thr Arg Leu Gln Ser Tyr Ser
145                 150                 155                 160

Glu Phe Ile Lys Ile Gly Glu Gln Thr His Tyr Thr Gly Val Trp Asn
                165                 170                 175

Gly Leu Val Thr Ile Phe Lys Thr Glu Gly Val Lys Gly Leu Phe Arg
            180                 185                 190

Gly Ile Asp Ala Ala Ile Leu Arg Thr Gly Ala Gly Ser Ser Val Gln
            195                 200                 205

Leu Pro Ile Tyr Asn Thr Ala Lys Asn Ile Leu Val Lys Asn Asp Leu
            210                 215                 220

Met Lys Asp Gly Pro Ala Leu His Leu Thr Ala Ser Thr Ile Ser Gly
225                 230                 235                 240

Leu Gly Val Ala Val Val Met Asn Pro Trp Asp Val Ile Leu Thr Arg
            245                 250                 255

Ile Tyr Asn Gln Lys Gly Asp Leu Tyr Lys Gly Pro Ile Asp Cys Leu
            260                 265                 270

Val Lys Thr Val Arg Ile Glu Gly Val Thr Ala Leu Tyr Lys Gly Phe
            275                 280                 285

Ala Ala Gln Val Phe Arg Ile Ala Pro His Thr Ile Met Cys Leu Thr
            290                 295                 300

Phe Met Glu Gln Thr Met Lys Leu Val Tyr Ser Ile Glu Ser Arg Val
305                 310                 315                 320

Leu Gly His Asn

<210> SEQ ID NO 5
<211> LENGTH: 298
<212> TYPE: PRT
<213> ORGANISM: Saccharomyces cerevisiae

<400> SEQUENCE: 5

Met Ala Gly Gly Leu Ala Ala Cys Ile Ala Val Thr Val Thr Asn Pro
1               5                   10                  15

Ile Glu Leu Ile Lys Ile Arg Met Gln Leu Gln Gly Glu Met Ser Ala
                20                  25                  30

Ser Ala Ala Lys Val Tyr Lys Asn Pro Ile Gln Gly Met Ala Val Ile
            35                  40                  45

Phe Lys Asn Glu Gly Ile Lys Gly Leu Gln Lys Gly Leu Asn Ala Ala
        50                  55                  60

Tyr Ile Tyr Gln Ile Gly Leu Asn Gly Ser Arg Leu Gly Phe Tyr Glu
65                  70                  75                  80

```
Pro Ile Arg Ser Ser Leu Asn Gln Leu Phe Pro Asp Gln Glu Pro
                85                  90                  95

His Lys Val Gln Ser Val Gly Val Asn Val Phe Ser Gly Ala Ala Ser
            100                 105                 110

Gly Ile Ile Gly Ala Val Ile Gly Ser Pro Leu Phe Leu Val Lys Thr
        115                 120                 125

Arg Leu Gln Ser Tyr Ser Glu Phe Ile Lys Ile Gly Glu Gln Thr His
    130                 135                 140

Tyr Thr Gly Val Trp Asn Gly Leu Val Thr Ile Phe Lys Thr Glu Gly
145                 150                 155                 160

Val Lys Gly Leu Phe Arg Gly Ile Asp Ala Ala Ile Leu Arg Thr Gly
                165                 170                 175

Ala Gly Ser Ser Val Gln Leu Pro Ile Tyr Asn Thr Ala Lys Asn Ile
            180                 185                 190

Leu Val Lys Asn Asp Leu Met Lys Asp Gly Pro Ala Leu His Leu Thr
        195                 200                 205

Ala Ser Thr Ile Ser Gly Leu Gly Val Ala Val Met Asn Pro Trp
    210                 215                 220

Asp Val Ile Leu Thr Arg Ile Tyr Asn Gln Lys Gly Asp Leu Tyr Lys
225                 230                 235                 240

Gly Pro Ile Asp Cys Leu Val Lys Thr Val Arg Ile Glu Gly Val Thr
                245                 250                 255

Ala Leu Tyr Lys Gly Phe Ala Ala Gln Val Phe Arg Ile Ala Pro His
            260                 265                 270

Thr Ile Met Cys Leu Thr Phe Met Glu Gln Thr Met Lys Leu Val Tyr
        275                 280                 285

Ser Ile Glu Ser Arg Val Leu Gly His Asn
    290                 295

<210> SEQ ID NO 6
<211> LENGTH: 528
<212> TYPE: PRT
<213> ORGANISM: Kluyveromyces lactis

<400> SEQUENCE: 6

Met Ala Ala Glu Ser Ile Val Ser Arg Asp Glu Ser Ile Ala Ser Leu
1               5                   10                  15

Glu Lys Ala Glu Gly Arg Ile Thr Tyr Leu Lys Pro Gln Ser Arg Ile
            20                  25                  30

Thr Trp Ser Asp Ala Lys Lys Tyr Leu Ala Thr Arg Ile Pro Thr Leu
        35                  40                  45

Phe Pro Thr Lys Ala Ser Ile Arg Glu Ala Arg Lys Glu Tyr Pro Ile
    50                  55                  60

Asn Pro Phe Pro Ala Leu Arg Ser Met Asn Trp Leu Gln Thr Gln Tyr
65                  70                  75                  80

Phe Ile Val Gly Phe Leu Ala Trp Thr Trp Asp Ala Leu Asp Phe Phe
                85                  90                  95

Ala Val Ser Leu Asn Met Thr Asn Leu Ala Lys Asp Leu Asp Arg Pro
            100                 105                 110

Val Lys Asp Ile Ser His Ala Ile Thr Leu Val Leu Leu Arg Val
        115                 120                 125

Ile Gly Ala Leu Ile Phe Gly Tyr Leu Gly Asp Arg Tyr Gly Arg Lys
    130                 135                 140

Tyr Ser Phe Val Leu Thr Met Ala Leu Ile Ile Val Ile Gln Ile Gly
145                 150                 155                 160
```

Thr Gly Phe Val Asn Ser Phe Ser Ala Phe Leu Gly Cys Arg Ala Ile
            165                 170                 175

Phe Gly Ile Ile Met Gly Ser Val Phe Gly Val Ala Ser Ala Thr Ala
            180                 185                 190

Leu Glu Asn Ala Pro Asn Lys Ala Lys Ser Ile Leu Ser Gly Ile Phe
            195                 200                 205

Gln Glu Gly Tyr Ala Phe Gly Tyr Leu Leu Gly Val Val Phe Gln Arg
        210                 215                 220

Ala Ile Val Asp Asn Ser Pro His Gly Trp Arg Ala Ile Phe Trp Phe
225                 230                 235                 240

Ser Ala Gly Pro Pro Val Leu Phe Ile Ala Trp Arg Leu Met Leu Pro
            245                 250                 255

Glu Ser Gln His Tyr Val Glu Arg Val Arg Leu Glu Lys Leu Glu Asn
            260                 265                 270

Asp Gly Lys Ser Gln Phe Trp Lys Asn Ala Lys Leu Ala Cys Ser Gln
            275                 280                 285

Tyr Trp Leu Ser Met Ile Tyr Leu Val Leu Leu Met Ala Gly Phe Asn
            290                 295                 300

Phe Ser His Gly Ser Gln Asp Leu Phe Pro Thr Met Leu Thr Ser
305                 310                 315                 320

Gln Tyr Gln Phe Ser Ala Asp Ala Ser Thr Val Thr Asn Ser Val Ala
            325                 330                 335

Asn Leu Gly Ala Ile Ala Gly Gly Ile Ile Val Ala His Ala Ser Ser
            340                 345                 350

Phe Phe Gly Arg Arg Phe Ser Ile Val Cys Cys Ile Gly Gly Gly
            355                 360                 365

Ala Met Leu Tyr Pro Trp Gly Phe Val Ala Asn Lys Ser Gly Ile Asn
            370                 375                 380

Ala Ser Val Phe Phe Leu Gln Phe Val Gln Gly Ala Trp Gly Ile
385                 390                 395                 400

Val Pro Ile His Leu Thr Glu Leu Ala Pro Thr Glu Phe Arg Ala Leu
            405                 410                 415

Ile Thr Gly Val Ala Tyr Gln Leu Gly Asn Met Ile Ser Ser Ala Ser
            420                 425                 430

Ser Thr Ile Glu Ala Ser Ile Gly Glu Arg Phe Pro Leu Glu Gly Arg
            435                 440                 445

Glu Asp Ala Tyr Asp Tyr Gly Lys Val Met Cys Ile Phe Met Gly Cys
450                 455                 460

Val Phe Ala Tyr Leu Leu Ile Val Thr Val Leu Gly Pro Glu Asn Lys
465                 470                 475                 480

Gly Gly Glu Leu Arg Leu Ser Thr Thr Gly Thr Glu Gln Asp Asp Glu
            485                 490                 495

Glu Ser Gln Asn Asn Ile Ser Phe Glu Ile Val Ala Ala Gly Pro
            500                 505                 510

Val Ser Asp Leu Asn Phe Lys Gln Glu Ile Gln His Lys Glu Arg Val
            515                 520                 525

<210> SEQ ID NO 7
<211> LENGTH: 527
<212> TYPE: PRT
<213> ORGANISM: Kluyveromyces dobzhanskii

<400> SEQUENCE: 7

Met Ala Ala Asp Ser Ile Val Ser Gln Glu Glu Ser Val Val Ser Tyr

-continued

```
1               5                    10                   15
Asp Lys Ala Glu Gly Arg Ile Thr Tyr Leu Lys Pro Gln Ser Gln Ile
                20                   25                   30
Thr Trp Ser Asp Ala Lys His Tyr Leu Gly Thr Arg Leu Pro Thr Leu
                35                   40                   45
Phe Pro Thr Lys Arg Ser Ile Lys Glu Ala Arg Lys His Tyr Pro Leu
                50                   55                   60
Asn Pro Phe Pro Ala Leu Arg Ser Met Asn Trp Leu Gln Thr Gln Tyr
65                   70                   75                   80
Phe Leu Val Gly Phe Leu Ala Trp Thr Trp Asp Ala Leu Asp Phe Phe
                    85                   90                   95
Ala Val Ser Leu Asn Met Thr Asn Leu Ala Arg Asp Leu Asp Arg Pro
                100                  105                  110
Val Lys Asp Ile Ser His Ala Ile Thr Leu Val Leu Leu Leu Arg Val
                115                  120                  125
Val Gly Ala Leu Ile Phe Gly Tyr Leu Gly Asp Arg Tyr Gly Arg Lys
                130                  135                  140
Tyr Ser Phe Val Ala Thr Met Val Leu Ile Val Ile Gln Ile Gly
145                 150                  155                  160
Thr Gly Phe Val Thr Thr Phe Ser Ala Phe Leu Gly Cys Arg Ala Ile
                    165                  170                  175
Phe Gly Ile Ile Met Gly Ser Val Phe Gly Val Ala Ser Ala Thr Ser
                180                  185                  190
Leu Glu Asn Ala Pro His Lys Ala Lys Ser Ile Leu Ser Gly Ile Phe
                195                  200                  205
Gln Glu Gly Tyr Ala Phe Gly Tyr Leu Leu Gly Val Val Phe Gln Arg
                210                  215                  220
Ala Ile Val Asp Asn Ser Pro His Gly Trp Arg Ala Met Phe Trp Phe
225                  230                  235                  240
Ser Ser Gly Pro Pro Val Leu Phe Ile Ala Trp Arg Leu Met Leu Pro
                    245                  250                  255
Glu Ser Gln His Tyr Leu Glu Arg Val Arg Leu Glu Lys Leu Glu Asn
                260                  265                  270
Asp Gly Glu Ser Gln Phe Trp Lys Asn Ala Lys Leu Ala Cys Ser Gln
                275                  280                  285
Tyr Trp Leu Ser Met Val Tyr Leu Val Leu Met Ala Gly Phe Asn
                290                  295                  300
Phe Ser Ser His Gly Ser Gln Asp Leu Phe Pro Thr Met Leu Thr Ser
305                  310                  315                  320
Gln Tyr Gln Phe Ser Ala Asp Ala Ser Thr Val Thr Asn Ser Val Ala
                    325                  330                  335
Asn Leu Gly Ala Ile Ala Gly Gly Ile Ile Val Ala His Ser Ser Ser
                340                  345                  350
Phe Ile Gly Arg Arg Phe Ala Ile Leu Leu Cys Cys Ile Gly Gly Gly
                355                  360                  365
Ala Met Leu Tyr Pro Trp Gly Phe Ile Ala Asn Lys Ser Gly Leu Asn
                370                  375                  380
Ala Ser Val Phe Phe Leu Gln Phe Phe Val Gln Gly Ala Trp Gly Ile
385                  390                  395                  400
Val Pro Ile His Leu Thr Glu Leu Ala Pro Ala Glu Phe Arg Ala Leu
                    405                  410                  415
Ile Thr Gly Val Ala Tyr Gln Leu Gly Asn Met Ile Ser Ser Ala Ser
                420                  425                  430
```

Ser Thr Ile Glu Ala Thr Leu Gly Glu Lys Phe Pro Ile Glu Gly Arg
            435                 440                 445

Glu Gly Ala Tyr Asp Tyr Gly Lys Val Met Cys Ile Phe Met Gly Cys
    450                 455                 460

Val Phe Ala Tyr Leu Leu Ile Ile Thr Val Leu Gly Pro Glu Asn Lys
465                 470                 475                 480

Gly Gly Glu Leu Arg Leu Ser Ser Pro Gly Met Glu Asp Asp Val Glu
            485                 490                 495

Ser Gln Asn Asn Val Ser Phe Glu Arg Val Gly Glu Ile Gln Pro Ala
            500                 505                 510

Ser Glu Leu Asn Phe Lys Gln Glu Phe Gln His Lys Glu Arg Val
            515                 520                 525

<210> SEQ ID NO 8
<211> LENGTH: 448
<212> TYPE: PRT
<213> ORGANISM: Rhizobium leguminosarum

<400> SEQUENCE: 8

Met Gly Ile Glu Leu Leu Ser Ile Gly Leu Leu Ile Ala Met Phe Ile
1               5                   10                  15

Ile Ala Thr Ile Gln Pro Ile Asn Met Gly Ala Leu Ala Phe Ala Gly
            20                  25                  30

Ala Phe Val Leu Gly Ser Met Ile Gly Met Lys Thr Asn Glu Ile
        35                  40                  45

Phe Ala Gly Phe Pro Ser Asp Leu Phe Leu Thr Leu Val Ala Val Thr
50                  55                  60

Tyr Leu Phe Ala Ile Ala Gln Ile Asn Gly Thr Ile Asp Trp Leu Val
65                  70                  75                  80

Glu Cys Ala Val Arg Leu Val Arg Gly Arg Ile Gly Leu Ile Pro Trp
                85                  90                  95

Val Met Phe Leu Val Ala Ala Ile Ile Thr Gly Phe Gly Ala Leu Gly
            100                 105                 110

Pro Ala Ala Val Ala Ile Leu Ala Pro Val Ala Leu Ser Phe Ala Val
            115                 120                 125

Gln Tyr Arg Ile His Pro Val Met Met Gly Leu Met Val Ile His Gly
130                 135                 140

Ala Gln Ala Gly Gly Phe Ser Pro Ile Ser Ile Tyr Gly Gly Ile Thr
145                 150                 155                 160

Asn Gln Ile Val Ala Lys Ala Gly Leu Pro Phe Ala Pro Thr Ser Leu
                165                 170                 175

Phe Leu Ser Ser Phe Phe Phe Asn Leu Ala Ile Ala Val Leu Val Phe
            180                 185                 190

Phe Val Phe Gly Gly Ala Arg Val Met Lys His Asp Pro Ala Ser Leu
        195                 200                 205

Gly Pro Leu Pro Glu Leu His Pro Glu Gly Val Ser Ala Ser Ile Arg
210                 215                 220

Gly His Gly Gly Thr Pro Ala Lys Pro Ile Arg Glu His Ala Tyr Gly
225                 230                 235                 240

Thr Ala Ala Asp Thr Ala Thr Thr Leu Arg Leu Asn Asn Glu Arg Ile
                245                 250                 255

Thr Thr Leu Ile Gly Leu Thr Ala Leu Gly Ile Gly Ala Leu Val Phe
            260                 265                 270

Lys Phe Asn Val Gly Leu Val Ala Met Thr Val Ala Val Val Leu Ala

```
            275                 280                 285
Leu Leu Ser Pro Lys Thr Gln Lys Ala Ala Ile Asp Lys Val Ser Trp
    290                 295                 300

Ser Thr Val Leu Leu Ile Ala Gly Ile Ile Thr Tyr Val Gly Val Met
305                 310                 315                 320

Glu Lys Ala Gly Thr Val Asp Tyr Val Ala Asn Gly Ile Ser Ser Leu
                325                 330                 335

Gly Met Pro Leu Leu Val Ala Leu Leu Leu Cys Phe Thr Gly Ala Ile
                340                 345                 350

Val Ser Ala Phe Ala Ser Ser Thr Ala Leu Leu Gly Ala Ile Ile Pro
            355                 360                 365

Leu Ala Val Pro Phe Leu Leu Gln Gly His Ile Ser Ala Ile Gly Val
    370                 375                 380

Val Ala Ala Ile Ala Ile Ser Thr Thr Ile Val Asp Thr Ser Pro Phe
385                 390                 395                 400

Ser Thr Asn Gly Ala Leu Val Val Ala Asn Ala Pro Asp Asp Ser Arg
                405                 410                 415

Glu Gln Val Leu Arg Gln Leu Leu Ile Tyr Ser Ala Leu Ile Ala Ile
                420                 425                 430

Ile Gly Pro Ile Val Ala Trp Leu Val Phe Val Val Pro Gly Leu Val
            435                 440                 445
```

```
<210> SEQ ID NO 9
<211> LENGTH: 255
<212> TYPE: PRT
<213> ORGANISM: Malonomonas rubra

<400> SEQUENCE: 9

Met Trp Asp Ile Leu Val Ala Gln Leu Thr Gln Asn Gly Leu Ile Thr
1               5                   10                  15

Ser Phe Val Ile Val Gly Val Thr Met Tyr Val Ala Tyr Met Leu Ser
                20                  25                  30

Ala Lys Leu Thr Lys Gly Lys Phe His Gly Ser Ala Ile Ala Ile Ile
            35                  40                  45

Leu Gly Leu Val Leu Ala Tyr Val Gly Gly Ala Ala Thr Asp Gly Gly
        50                  55                  60

Ser Lys Gly Leu Ala Ser Ile Pro Met Phe Ala Gly Val Gly Leu Met
65                  70                  75                  80

Gly Gly Ser Met Leu Arg Asp Leu Ala Ile Val Ala Thr Ser Phe Gly
                85                  90                  95

Val Asp Leu Arg Glu Val Lys Lys Ser Gly Leu Ser Gly Thr Val Ser
                100                 105                 110

Leu Phe Met Gly Ile Phe Val Ser Phe Phe Ile Gly Ala Gly Met Ala
            115                 120                 125

Ile Ala Phe Gly Tyr Thr Asp Ala Val Ser Ile Thr Thr Ile Gly Ala
        130                 135                 140

Gly Ala Val Thr Tyr Ile Val Gly Pro Val Thr Gly Ala Ala Val Gly
145                 150                 155                 160

Ala Asp Ser Ala Val Ala Leu Ser Val Ala Ala Gly Leu Val Lys
                165                 170                 175

Ser Ile Leu Val Met Thr Ser Thr Pro Leu Phe Ala Lys Ile Val Gly
            180                 185                 190

Leu Asp Asn Pro Asn Ser Ala Met Val Phe Gly Gly Leu Met Gly Thr
        195                 200                 205
```

```
Thr Ser Gly Val Thr Ala Gly Leu Ala Ala Thr Asn Pro Lys Leu Val
    210                 215                 220

Pro Tyr Gly Ala Met Thr Ser Thr Phe Tyr Thr Gly Leu Gly Cys Leu
225                 230                 235                 240

Leu Cys Pro Ser Val Leu Phe Leu Leu Met Lys Gly Ile Tyr Gly
                245                 250                 255
```

<210> SEQ ID NO 10
<211> LENGTH: 254
<212> TYPE: PRT
<213> ORGANISM: Pseudomonas putida

<400> SEQUENCE: 10

```
Met Trp Pro Ile Ile Glu Asn Ala Leu Glu His Asn Gly Leu Ile Thr
1               5                   10                  15

Ala Phe Ala Val Val Gly Ala Ile Met Trp Leu Ser Val Leu Leu Ser
                20                  25                  30

Lys Tyr Leu Thr Phe Gly Arg Val His Gly Ser Ala Ile Ala Ile Val
            35                  40                  45

Ile Gly Leu Val Leu Ala Trp Val Gly Gly Thr Val Thr Gly Gly Gln
    50                  55                  60

Lys Gly Leu Ala Asp Met Ala Leu Phe Ser Gly Ile Gly Leu Met Gly
65                  70                  75                  80

Gly Ala Met Leu Arg Asp Phe Ile Val Ala Thr Ala Phe Glu Val
                85                  90                  95

Gln Ala Thr Glu Ala Arg Lys Ala Gly Met Ile Gly Ala Val Ala Leu
            100                 105                 110

Leu Leu Gly Thr Val Leu Pro Phe Ile Val Gly Ala Ala Val Ala Tyr
        115                 120                 125

Ala Phe Gly Tyr Arg Asp Ala Val Ser Met Thr Thr Ile Gly Ala Gly
    130                 135                 140

Ala Val Thr Tyr Ile Val Gly Pro Val Thr Gly Ala Ala Leu Gly Ala
145                 150                 155                 160

Ser Ser Asp Val Met Ala Leu Ser Ile Ala Thr Gly Leu Ile Lys Ala
                165                 170                 175

Ile Leu Val Met Val Phe Thr Pro Val Ser Ala Arg Leu Leu Ala Leu
            180                 185                 190

Asp Asn Pro Arg Ser Ala Met Val Phe Gly Gly Leu Ala Gly Thr Val
        195                 200                 205

Ser Gly Val Thr Ala Gly Leu Ala Ala Thr Asp Arg Arg Leu Val Pro
    210                 215                 220

Tyr Gly Ala Leu Thr Ala Thr Phe His Thr Gly Leu Gly Cys Leu Met
225                 230                 235                 240

Gly Pro Ser Ile Leu Tyr Phe Cys Ile Arg Gly Leu Val Gly
                245                 250
```

<210> SEQ ID NO 11
<211> LENGTH: 129
<212> TYPE: PRT
<213> ORGANISM: Malonomonas rubra

<400> SEQUENCE: 11

```
Met Val Ile Tyr Gly Val Ala Leu Leu Ser Gly Cys Phe Leu Val Gly
1               5                   10                  15

Lys Val Thr Gly Ser Trp Leu Gly Ala Ala Ile Gly Val Lys Ala Asn
                20                  25                  30
```

```
Val Gly Gly Val Gly Ile Ser Met Leu Leu Val Ile Val Cys Asp
            35              40              45

Ile Leu Ile Lys Lys Gly Lys Leu Lys Gln Leu Ser Gln Asp Gly Ile
        50              55              60

Gly Phe Trp Asn Ala Met Tyr Ile Pro Ile Val Val Ala Met Ala Ala
65              70              75              80

Lys Gln Asn Val Ile Gly Ala Ile Asp Gly Gly Trp Leu Ala Leu Leu
                85              90              95

Ala Gly Gly Val Ala Thr Val Val Ser Tyr Phe Met Ile Pro Val Ile
            100             105             110

Ser Lys Leu Gly Gln Gly Thr Lys Val Pro Ala Ile Glu Glu Pro Ser
        115             120             125

Ser

<210> SEQ ID NO 12
<211> LENGTH: 163
<212> TYPE: PRT
<213> ORGANISM: Pseudomonas putida

<400> SEQUENCE: 12

Met Met Ala Gly Leu Arg Met Ala Lys Asn Asn Asn Lys Gln Leu Arg
1               5                   10                  15

His Tyr Leu Arg Thr Thr Thr Met Ile Ile Tyr Gly Val Ala Leu Leu
            20                  25                  30

Ala Val Cys Thr Leu Ala Gly Val Ile Val Gly Asp Phe Leu Gly Val
            35              40              45

Leu Leu Gly Val Lys Ser Asn Val Gly Gly Val Gly Ile Ala Met Ile
        50              55              60

Leu Leu Ile Cys Ala Arg Leu Tyr Met His Arg Asn Gly Gly Met Ser
65              70              75              80

Lys Glu Cys Glu Phe Gly Val Gly Phe Trp Gly Ala Met Tyr Ile Pro
                85              90              95

Val Val Val Ala Met Ala Ala Gln Gln Asn Val Val Thr Ala Leu His
            100             105             110

Gly Gly Pro Val Ala Leu Leu Ala Ala Val Gly Ala Val Leu Val Cys
            115             120             125

Gly Leu Thr Ile Ala Leu Ile Ser Arg Ser His Arg Gly Glu Pro Leu
        130             135             140

Pro Ala Leu Glu Pro Ser Pro Glu Thr Gln Ala Gln Val Ala Pro Ala
145             150             155             160

Gly Gly Arg
```